(12) United States Patent
Chiba et al.

(10) Patent No.: US 8,076,449 B2
(45) Date of Patent: Dec. 13, 2011

(54) THERAPEUTIC AGENTS OF COLIVELIN FOR NEURODEGENERATIVE DISEASES

(75) Inventors: Tomohiro Chiba, Tokyo (JP); Yoshiko Kita, Tokyo (JP); Masaaki Matsuoka, Tokyo (JP); Kenzo Terashita, Tokyo (JP); Sadakazu Aiso, Tokyo (JP); Ikuo Nishimoto, Chiba (JP); Tomo Nishimoto, legal representative, Chiba (JP)

(73) Assignees: Tomohiro Chiba, Tokyo (JP); Massaaki Matsuoka, Tokyo (JP); Kenzo Terashita, Tokyo (JP); Sadakazu Also, Tokyo (JP); Tomo Nishimoto, Ichikawa-shi (JP)

( * ) Notice: Subject to any disclaimer, the term of this patent is extended or adjusted under 35 U.S.C. 154(b) by 542 days.

(21) Appl. No.: 11/578,142

(22) PCT Filed: Apr. 8, 2005
(Under 37 CFR 1.47)

(86) PCT No.: PCT/JP2005/007286
§ 371 (c)(1),
(2), (4) Date: Dec. 3, 2007

(87) PCT Pub. No.: WO2005/097156
PCT Pub. Date: Oct. 20, 2005

(65) Prior Publication Data
US 2008/0227699 A1    Sep. 18, 2008

Related U.S. Application Data

(60) Provisional application No. 60/560,254, filed on Apr. 8, 2004.

(51) Int. Cl.
*A61K 38/16* (2006.01)
*A61K 38/00* (2006.01)
*A61K 38/18* (2006.01)
*C07K 14/00* (2006.01)
*C07K 17/00* (2006.01)

(52) U.S. Cl. ............ 530/300; 514/1.1; 514/1.2; 514/1.3
(58) Field of Classification Search .................. None
See application file for complete search history.

(56) References Cited

U.S. PATENT DOCUMENTS

| 6,174,862 B1 | 1/2001 | Brenneman | |
| 6,613,740 B1 | 9/2003 | Gozes et al. | |
| 7,314,864 B1 * | 1/2008 | Nishimoto | 514/12 |
| 2005/0233413 A1 * | 10/2005 | Nishimoto et al. | 435/69.1 |
| 2008/0102055 A1 * | 5/2008 | Chiba et al. | 424/85.2 |
| 2009/0075900 A1 * | 3/2009 | Aiso et al. | 514/15 |

FOREIGN PATENT DOCUMENTS

| EP | 1221480 | * | 3/2001 |
| JP | 2001-522228 A | | 11/2001 |
| WO | WO-00/53217 A2 | | 9/2000 |
| WO | WO-01/12654 A2 | | 2/2001 |
| WO | WO-01/21787 A1 | | 3/2001 |
| WO | WO-01/92333 A2 | | 12/2001 |
| WO | WO-03/097687 A2 | | 11/2003 |
| WO | WO-2004/060309 A2 | | 7/2004 |
| WO | WO-2004/080957 A2 | | 9/2004 |

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Chiba, T. et al., "Development of a Femtomolar-Acting Humanin Derivative Named Colivelin by Attaching Activity-Dependent Neurotrophic Factor to Its N Terminus: Characterization of Colivelin-Mediated Neuroprotection against Alzheimer's Disease-Relevant Insults in Vitro and in Vivo," The Journal of Neuroscience: The Official Journal of the Society for Neuroscience, vol. 25, No. 44, pp. 10252-10261, Nov. 2, 2005, XP-002532185.
Supplementary Partial European Search Report for corresponding European Application No. 05730322.4 mailed Jun. 29, 2009.
Don W. Cleveland et al., *Neuroscience*, vol. 2, (Nov. 2001), pp. 806819.
Collette K. Hand, PhD. et al., *Muscle & Nerve*, (Feb. 2002), pp. 135-159.
Lewis P. Rowland, M.D, et al., *The New England Journal of Medicine*, vol. 344, No. 22, (May 31, 2001), pp. 1688-1701.
Martin R. Turner et al., *Seminars in Neurology*, vol. 21, No. 2, (2001), pp. 167-175.
Robert G. Miller, M.D. at al., *Annals of Neurology*, vol. 39, No. 2, (Feb. 1996), pp. 256-0261.
Daniel R. Rosen et al., *Nature*, vol. 362, (Mar. 4, 1993), 59-62.
Shahrooz Rabizadeh et al., *Proc. Natl. Acad. Sci.*, vol. 92, (Mar. 1995), pp. 3024-3028.
H.D. Durham, PhD. et al., *Journal of Neuropathology and Experimental Neurology*, vol. 56, No. 5, (May 1997), pp. 523-530.
C.D. Ghadge et al., *The Journal of Neuroscience*, vol. 17, No. 22, (Nov. 15, 1997), pp. 8756-8766.
Vladimir Kostic et al., *Science*, vol. 277, (Jul. 25, 1997), pp. 559-562.
Mimoun Azzouz et al., *Human Molecular Genetics*, vol. 9, No. 5, (2000), pp. 803-811.
Mingwei Li et al., *Science*, vol. 288, (Apr. 14, 2000), pp. 335-339.
Kohsuke Kanekura et al, *The Journal of Biological Chemistry*, vol. 279, No. 18, (Apr. 30, 2004), pp. 19247-19256.

(Continued)

*Primary Examiner* — Chang-Yu Wang
(74) *Attorney, Agent, or Firm* — Birch, Stewart, Kolasch & Birch, LLP.

(57) ABSTRACT

The present invention relates to a pharmaceutical composition for the treatment and/or prevention of a neurodegenerative disease, comprising the following polypeptide shown in any of (a) to (c): (a) a polypeptide comprising the amino acid sequence represented by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1); (b) a polypeptide comprising an amino acid sequence having a deletion, substitution, insertion, and/or addition of one or several amino acids in the amino acid sequence consisting of Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), and having an activity that inhibits neuronal cell death associated with neurodegenerative disease; and (c) a modified polypeptide from the polypeptide (a) or (b), or a pharmaceutically acceptable salt thereof, as an effective ingredient.

7 Claims, 10 Drawing Sheets
(2 of 10 Drawing Sheet(s) Filed in Color)

OTHER PUBLICATIONS

Barkur S. Shastry et al., *Brain Research Bulletin*, vol. 48, No. 2, (1999), pp. 121-127.
B. Zhao et al., *Journal of Neuroscience Research*, vol. 47, (1997), pp. 253-263.
Jin-Jun Luo et al, *Journal of Neuroscience Research*, vol. 55, (1999), pp. 629-642.
Benjamin Wolozin et al., *Science*, vol. 274, (Dec. 6, 1996), pp. 1710-1713.
Wolozin et al., *Neurobiology of Aging*, vol. 19, No. 15, (1998), pp. S23-S27.
Qing Guo et al., *NeuroReport*, vol. 8, (1996), pp. 379-383.
Zhuohua Zhang et al., *Nature*, vol. 395, (Oct. 15, 1998), pp. 698-702.
Qing Guo et al., *Proc. Natl. Acad. Sci. USA*, vol. 96, (Mar. 1999), pp. 4125-4130.
C. Chech et al., *Neuroscience*, vol. 87, No. 2, (1998), pp. 325-336.
Conrad C. Weihl et al., *The Journal of Neuroscience*, vol. 19, No. 13, (Jul. 1, 1999), pp. 5360-5369.
Sherry Bursztajn et al., *The Journal of Neuroscience*, vol. 18, No. 23, (Dec. 1, 1998), pp. 9790-9799.
T. Yamatsuji et al., *Science*, vol. 272, (1996), pp. 1349-1352.
Hashimoto et. al., The Jornal of Neuroscience vol. 21, No. 23, pp. 9235-9245 (Dec. 1, 2001).
Terashita et al., Journal of Neurochemistry vol. 85, pp. 1521-1538 (2003).
Zamostiano et al., "A femtomolar-acting neuroprotective peptide induces increased levels of heat shock protein 60 in rat cortical neurons: a potential neuroprotective mechanism," Neuroscience Letters, vol. 264, 1999, pp. 9-12.
Brenneman et al., "Activity-Dependent Neurotrophic Factor: Structure-Activity Relationships of Femtomolar-Acting Peptides[1]," The Journal of Pharmacology and Experimental Therapeutics, vol. 285, No. 2, 1998, pp. 619-627.
Notice of References Cited in a U.S. Office Action dated Jan. 7, 2010, for related U.S. Appl. No. 11/578,141.

* cited by examiner

Fig. 6
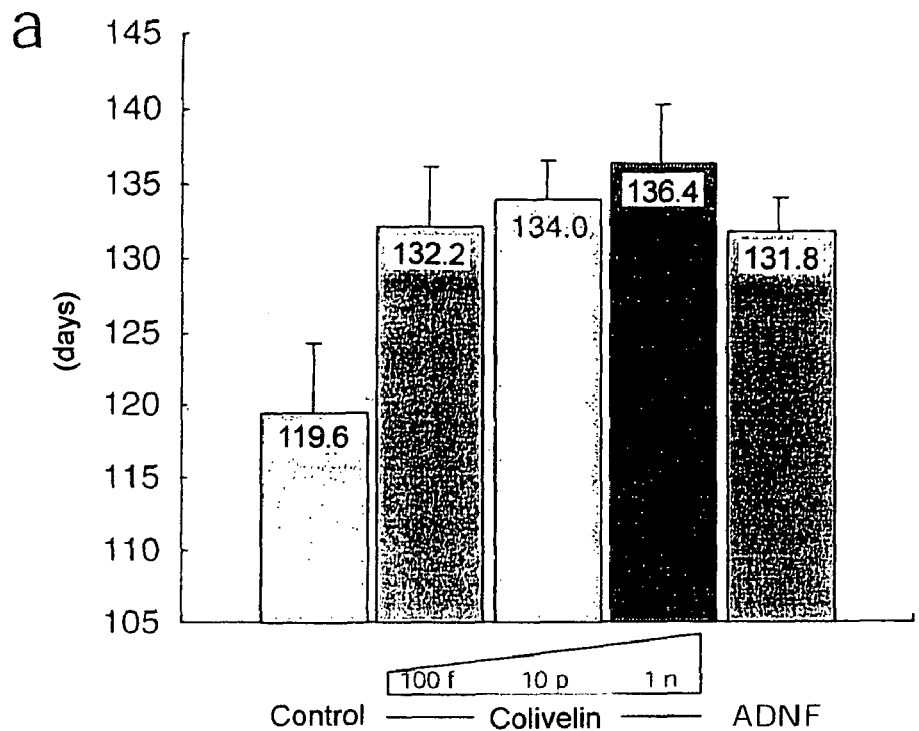
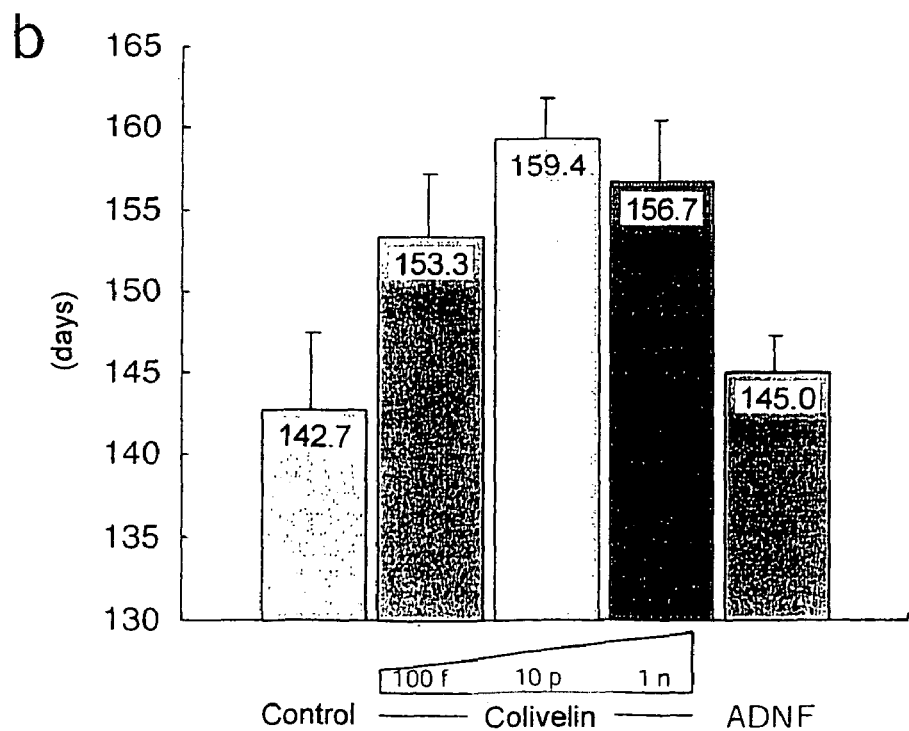

THERAPEUTIC AGENTS OF COLIVELIN FOR NEURODEGENERATIVE DISEASES

CROSS-REFERENCE TO RELATED APPLICATIONS

This application is the national phase of PCT application PCT/JP2005/007286 filed on Apr. 8, 2005 and claims priority under 35 U.S.C. 119(e) on U.S. Provisional Application No(s). 60/560,254 filed on Apr. 8, 2004; the entire contents of all are hereby incorporated by reference.

BACKGROUND OF THE INVENTION

1. Field of the Invention

The present invention relates to a therapeutic and/or preventive agent for neurodegenerative diseases such as Alzheimer's disease and amyotrophic lateral sclerosis.

2. Description of Related Art

Neurodegenerative diseases are caused by the selective death (apoptosis) of particular neurons, triggered by characteristic abnormal protein accumulation in the neurons and so on. In some cases of neurodegenerative diseases, genetically defined abnormalities contribute to the development of the disease. The neurodegenerative diseases here include cerebral degenerative disease (e.g., Alzheimer's disease, Parkinson's disease, progressive supranuclear palsy, and Huntington's disease) and spinal degenerative disease/motor neuron degenerative disease (e.g., amyotrophic lateral sclerosis and spinal muscular atrophy).

Amyotrophic lateral sclerosis (ALS) is a neurodegenerative disease with selective loss of motor nerves in the cerebrum, brain stem, and spinal cord that typically affects people of middle or advanced age (Cleveland D W and Rothstein J D, 2001, Nat Rev Neurosci 2: 806-819; and Hand C K and Rouleau G A, 2002, Muscle Nerve 25: 135-159). ALS causes muscular atrophy and muscular weakness in voluntary muscles in the whole body except for extraocular muscles and eventually causes respiratory failure. Patients suffering from ALS usually die in 3 to 5 years from the onset.

Riluzole is the sole drug previously approved for ALS in US and Japan. Riluzole was originally developed as an anticonvulsant inhibiting glutamate release and has been reported in several clinical trials to exhibit only slight efficacy for the survival of ALS patients (Rowland L P and Shneider N A, 2001, N Engl J Med, 344, 1688-1700; and Turner M R and Parton M J, 2001, Semin Neurol 21: 167-175). In addition to riluzole, various factors including ciliary neurotrophic factor (CNTF) and insulin-like growth factor I (IGF-I) were tested in clinical trials and however, fell short of success (Miller R G et al., 1996, Ann Neurol 39: 256-260). Thus, there are currently no therapeutic agents effective for ALS under present circumstances.

Approximately 10% of ALS cases are familial (FALS) and with mostly autosomal-dominant inheritance. In 1993, Rosen et al identified for the first time the superoxide dismutase-1 (SOD1) gene located on the chromosome 21 as a causative gene by the analysis of pedigree with autosomal inheritance (Rosen D R, et al., 1993, Nature 362: 59-62). Approximately 20% of FALS cases are caused by mutations in the SOD1 gene, and most of these mutations are missense point mutations. More than one hundred SOD1 mutations have been found to cause FALS (Cleveland D W and Rothstein L D, supra). Several groups have reported that overexpression of FALS-associated SOD1 mutant genes induces neuronal cell death in vitro (e.g., Rabizadeh S, et al., 1995, Proc Natl Acad Sci USA 92: 3024-3028; Durham H D et al., 1997, J Neropathol Exp Neurol 56: 523-530; and Ghadge G D et al., 1997 J Nerosci 17: 8756-8766). Besides this, the activation of caspase-3 has been observed in the spinal cords in ALS patients. Taken altogether, the inhibition of neuronal cell death is an effective way for the development of therapeutic agents for ALS.

In addition to CNTF and IGF-I described above, Bcl2, a non-specific caspase inhibitor zVAD-fmk (Kostic V, et al., 1997, Science 277: 559-562; Azzouz M, et al., 2000, Hum Mol Genet. 9: 803-811; and Li M, et al., 2000, Science 288: 335-339), and alsin, the newly identified product of the ALS2 gene whose missense mutations cause recessive-inherited FALS (Kanekura K, et al, 2004, J Biol Chem 279: 19247-19256), have been reported to antagonize neuronal cell death caused by the overexpression of SOD1 mutants.

Alzheimer's disease (AD) is clinically characterized by progressive amnesia and cognitive impairment, and pathologically by extensive neuronal loss, intraneuronal tangles, and extracellular senile plaques whose cores have a high affinity to Congo red. There are no effective therapies for AD. It has been generally accepted that the clinical manifestation of this disease can be mostly explained by progressive neuronal cell death. Therefore, it is essential for the development of effective therapies against AD to elucidate the mechanisms underlying neuronal cell death in AD.

There are three different genes whose mutations cause early-onset familial AD (FAD). Three genes encodes APP (APP refers to amyloid precursor protein $APP_{695}$), presenilin (PS)-1, and PS2 (Shastry, B S and Giblin, F J, 1999, Brain Res. Bull. 48: 121-127). Yamatsuji et al have indicated that three FAD-linked APP mutants with mutations on the V642 positions cause neuronal death (Yamatsuji, T et al., 1996, Science 272: 1349-1352). This notion was verified by several groups that performed similar experiments using primary cultured neurons or other neuronal cell lines (Zhao, B et al., 1997, J. Neurosci. Res. 47: 253-263; and Luo, J et al., 1999, J. Neurosci. Res. 55: 629-42). In addition, Wolozin et al found that expression of FAD-associated mutant N141I PS-2 significantly induced death of PC12 cells, and that expression of FAD-associated mutant PS-1 induces apoptosis in T lymphocytes (Wolozin, B et al., 1996, Science 274: 1710-1713; and Wolozin, B et al., 1998, Neurobiol. Aging 19: S23-27). It has also been observed that expression of FAD-linked PS-1 mutants sensitizes neurons to death caused by $A\beta$ or lack of a trophic factor (Guo, Q et al., 1996, Neuroreport 8: 379-83; Zhang, Z et al., 1998, Nature 395: 698-702; and Guo, Q et al., 1999, Proc. Natl. Acad. Sci. USA 96: 4125-30), and that cultured cortical neurons derived from transgenic rats overexpressing wild-type PS-1 are more sensitive than non-transgenic controls to cell death caused by lack of a trophic factor (Czech, C et al., 1998, Neuroscience 87: 325-36). It has also been experimentally suggested that PS-1 mutants cause neuronal cell death (Weihl, C C et al., 1999, J. Neurosci. 19: 5360-9; and Bursztajn, S et al., 1998. J. Neurosci. 18: 9790-9). Thus, it is concluded that expression of all four types of FAD genes (V642 APP mutant, NL-APP, PS-1 mutant, and PS-2) induce neuronal cell death or sensitize neurons to death caused by other insults. Therefore, from the standpoint of neuronal death, the most important key for the development of AD therapies is to find a molecule that can suppress cell death induced by AD genes.

Huntington's disease (HD) is a neurodegenerative disease whose predominant manifestations consist of chronic progressive involuntary choreiform movements and dementia. Most HD cases are inherited in an autosomal-dominant fashion. Intellectual and psychiatric disorders seen in this disease are originated from extensive atrophy in the cerebral cortex, and pathological changes causing choreiform movements have been thought to be caused by atrophy of the corpus striatum, particularly by that of the nucleus caudatus. The HD pathogenesis has been investigated from the standpoint of amine metabolism and extrapyramidal syndrome in brain. A nucleotide sequence encoding polyglutamine on chromosome 4 provides a key to the HD pathogenesis. A glutamine-encoding triplet-nucleotide CAG is normally repeated 10 to 35 times (17 times on average). In HD cases, disease-causative proteins contain polygultamine regions consisting of 37 or more glutamines. Such abnormal proteins accumulate in neurons and promote cell death. Neurons in the corpus striatum are degenerated in HD. They include inhibitory neurons that originally send fibers to the substantia nigra or globus pallidus and release a neurotransmitter γ-aminobutyric acid (GABA) as well as excitatory neurons that send fibers to the same sites and release a neurotransmitter substance P. In addition, interneurons with short fibers in the corpus striatum, which use acetylcholine as a neurotransmitter, are partially degenerated. The degeneration of dopaminergic neurons projecting fibers from the substantia nigra to the corpus striatum causes the dysfunction of the extrapyramidal system. HD patients usually die of infectious disease or respiratory disorder accompanying dysphagia in 10 to 15 years since the disease onset.

ADNF or ADNF9 (activity-dependent neurotrophic factor), which consists of nine amino acid residues (Ser-Ala-Leu-Leu-Arg-Ser-Ile-Pro-Ala (SEQ ID NO: 5)), was originally purified by Gozes et al from the culture medium of astrocytes stimulated with VIP (Brenneman D E and Gozes I, 1996, J Clin Invest 97: 2299-2307; Brenneman D E, et al., 1998, J Pharmacol Exp Ther 285: 619-627; and Blondel O, et al., 2000, J Neurosci 20: 8012-8020). ADNF has been shown to protect neurons from neuronal cell death caused by some neurotoxic insults including amyloid β (Brenneman D E, et al., 1998, J Pharmacol Exp Ther 285: 619-627; and Glazner G W, et al., 2000, J Neurochem 73: 2341-2347). ADNF is a unique neuroprotective factor in that it has the neuroprotective activity at its lower concentrations from the femtomolar (fM) to picomolar (pM) order, and loses the activity at concentrations higher than the nanomolar (nM) order. Such unique but unfavorable property of ADNF have prevented it from being developed as an anti-Alzheimer's disease (AD) drug.

We have previously discovered a gene that encodes a 24-amino-acid peptide named Humanin (HN), using a cDNA library constructed from the brain tissues of AD patients. HN protects neurons from V642I APP-induced death. HN also suppresses all tested other types of neuronal cell death related to AD, that is, neuronal cell death induced by all known FAD genes and Aβ(1-43), while it does not show the rescue effect against neurotoxicity caused by polyglutamine repeats associated with Huntington's disease, spinocerebellar ataxia, or by amyotrophic lateral sclerosis-associated SOD1 mutants. We have further found that an HN derivative whose serine residue at the position 14 is replaced by glycine or D-serine has 1000-fold potent neuroprotective activity (International Publication No. WO 01/21787 A1; Hashimoto, Y et al., 2001, J. Neurosci., 21: 9235-9245; and Terashita, K et al., 2003, J. Neurochem., 85: 1521-1538).

Under these circumstances, we have conducted extensive studies to develop potent HN- and ADNF-derived therapeutic peptides protective against various neurodegenerative diseases, and have finally found a polypeptide named colivelin that is effective for the treatment of multiple neurodegenerative diseases including AD and amyotrophic lateral sclerosis.

BRIEF SUMMARY OF THE INVENTION

The present invention has the following characteristics:

In the first aspect, the present invention provides a pharmaceutical composition for the treatment and/or prevention of a neurodegenerative disease, comprising a polypeptide shown in any of (a) to (c):

(a) a polypeptide comprising the amino acid sequence represented by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1);

(b) a polypeptide comprising an amino acid sequence having a deletion, substitution, insertion, and/or addition of one or several amino acids in the amino acid sequence consisting of Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), and having an activity that inhibits neuronal cell death associated with neurodegenerative disease; and (c) a modified polypeptide from the polypeptide (a) or (b), or a pharmaceutically acceptable salt thereof, as an effective ingredient.

According to one embodiment, the polypeptide comprises an amino acid sequence represented by the following formula: Ser-Ala-Leu-Leu-Arg-Ser-Ile-Pro-Ala-Pro-$Xn_1$-(Cys, Arg, Lys, or His)-(Leu or Arg)-$Xn_2$-Leu-Thr-(Gly, L-Ser, or D-Ser)-$Xn_3$-Pro (SEQ ID NO: 2),
wherein $Xn_1$ comprises an amino acid sequence consisting of (Arg or Ala)-(Gly or Ala)-(Phe or Ala)-(Ser or Ala), $Xn_2$ comprises an amino acid sequence consisting of (Leu or Ala)-(Leu or Ala), and $Xn_3$ comprises an amino acid sequence represented by (Glu or Ala)-(Ile or Ala)-(Asp or Ala)-(Leu or Ala).

According to another embodiment, the polypeptide is a dimer.

According to a further embodiment, the polypeptide is a fusion with another peptide or polypeptide.

According to a further embodiment, the neurodegenerative disease is Alzheimer's disease or motor neuron degenerative disease.

According to a further embodiment, the motor neuron degenerative disease is amyotrophic lateral sclerosis.

In the second aspect, the present invention provides a polypeptide comprising the amino acid sequence represented by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), a modified polypeptide thereof, or a salt thereof.

According to one embodiment, the polypeptide of the present invention is a dimer.

According to another embodiment, the polypeptide of the present invention is a fusion with another peptide or polypeptide.

In the third aspect, the present invention provides a polypeptide comprising an amino acid sequence having a deletion, substitution, insertion, and/or addition of one or several amino acids in the amino acid sequence of Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), and having an activity that inhibits neuronal cell death associated with neurodegenerative disease, a modified polypeptide thereof, or a salt thereof.

According to one embodiment, the polypeptide of the present invention comprises an amino acid sequence represented by the following formula: Ser-Ala-Leu-Leu-Arg-Ser- Ile-Pro-Ala-Pro-Xn$_1$-(Cys, Arg, Lys, or His)-(Leu or Arg)-Xn$_2$-Leu-Thr-(Gly, L-Ser, or D-Ser)-Xn$_3$-Pro (SEQ ID NO: 2),
wherein Xn$_1$ comprises an amino acid sequence consisting of (Arg or Ala)-(Gly or Ala)-(Phe or Ala)-(Ser or Ala) (SEQ ID NO: 3), Xn$_2$ comprises an amino acid sequence consisting of (Leu or Ala)-(Leu or Ala), and Xn$_3$ comprises an amino acid sequence consisting of (Glu or Ala)-(Ile or Ala)-(Asp or Ala)-(Leu or Ala) (SEQ ID NO: 4).

According to another embodiment, the polypeptide of the present invention is a dimer.

According to a further embodiment, the polypeptide of the present invention is a fusion with another peptide or polypeptide.

In the fourth aspect, the present invention provides DNA encoding any of the polypeptides.

In the fifth aspect, the present invention provides an expression vector comprising the DNA.

In one embodiment, the vector of the present invention is used for therapy.

In another embodiment, the vector of the present invention is a viral vector.

In the sixth aspect, the present invention provides a host cell transformed with any of the expression vectors.

In the seventh aspect, the present invention provides a method for producing the polypeptide of the present invention, comprising culturing the host cell and collecting an expressed polypeptide from the host cell or culture supernatant thereof.

In the eighth aspect, the present invention provides a method for treating or preventing a neurodegenerative disease, comprising administering the polypeptide of the present invention to a subject to suppress neuronal cell death.

According to the present invention, the polypeptide of the present invention significantly suppresses neuronal cell death and has the effect of delaying the onset of a neurodegenerative disease such as amyotrophic lateral sclerosis (ALS) or Alzheimer's disease, the effect of improving the motor function of a subject, and the effect of prolonging the life span of a subject.

DEFINITION

Terms used herein have the following definitions:

"Neurodegenerative disease" is a progressive disease that degenerates and/or loses neurons and refers to a disease caused by the involvement of genetic factors or the cell death (apoptosis) of neurons attributed to abnormal protein accumulation and so on. Examples of the neurodegenerative disease include, but not limited to, cerebral degenerative diseases (e.g., Alzheimer's disease (AD), Parkinson's disease, progressive supranuclear palsy, and Huntington's disease (HD)), and spinal degenerative disease/motor neuron degenerative diseases (e.g., amyotrophic lateral sclerosis (ALS), spinal muscular atrophy, and spinocerebellar ataxia).

"Treatment" means the cure, alleviation, or suppression of conditions of a subject with neurodegenerative disease.

"Prevention" means the preclusion, protection, or inhibition of a subject from being affected with neurodegenerative disease.

"Activity that inhibits neuronal cell death" means the activity of the polypeptide of the present invention as an effective ingredient to inhibit, antagonize, or suppress neuronal cell death associated with neuronal degeneration and/or loss in neurodegenerative disease or the enhancement of neurotoxicity leading to the neuronal cell death. Neuronal cell death, for example, in ALS, is induced by, for example, mutant superoxide dismutase-1 (SOD1). Alternatively, neuronal cell death in AD is induced by, for example, mutant APP, PS-1, or PS-2, or by β-amyloid (Aβ), while in HD, it is induced by, for example, mutation of the polyglutamine repeat.

A "polypeptide" or "peptide" means a chain of amino acid residues, which comprises two or more L- and/or D-amino acids bound via amide linkage. In this specification, where the number of amino acid residues is relatively large then the chain is referred to as polypeptide; on the other hand, where the number of amino acid residues is relatively small then the chain is referred to as peptide, for the sake of convenience.

The term "pharmaceutically acceptable" is used for, for example, acids or bases for forming salts, carriers, and additives, generally acceptable in pharmaceutical industries.

"Modification" refers to a chemical modification of polypeptides, for example acetylation, acylation, pegylation, phosphorylation, sulfation, amidation, and glycosylation.

The "fusion" means a fusion of the polypeptide of the present invention with another polypeptide. Examples of another polypeptide include signal peptides and tag peptides (e.g., His tag and GFP).

The "subject" refers to a mammal including human, preferably human.

"Colivelin" refers to a polypeptide consisting of the amino acid sequence represented by SEQ ID NO: 1 and is also referred to as ADNF-AGA-C8R-HNG17 in Examples below.

"ADNF" is an abbreviation of Activity-Dependent Neurotrophic Factor and refers to a peptide consisting of the amino acid sequence represented by Ser-Ala-Leu-Leu-Arg-Ser-Ile-Pro-Ala (SEQ ID NO: 5).

"AGA-C8R-HNG17" refers to a peptide consisting of the amino acid sequence represented by Pro-Ala-Gly-Ala-Ser-Arg-Leu-Leu-Leu-Leu-Thr-Gly-Glu-Ile-Asp-Leu-Pro (SEQ ID NO: 6).

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 6 shows the effect of colivelin on the ALS onset (FIG. 6a) and survival lengths (FIG. 6b) of G93A-SOD1 transgenic mice;

Figure 1:
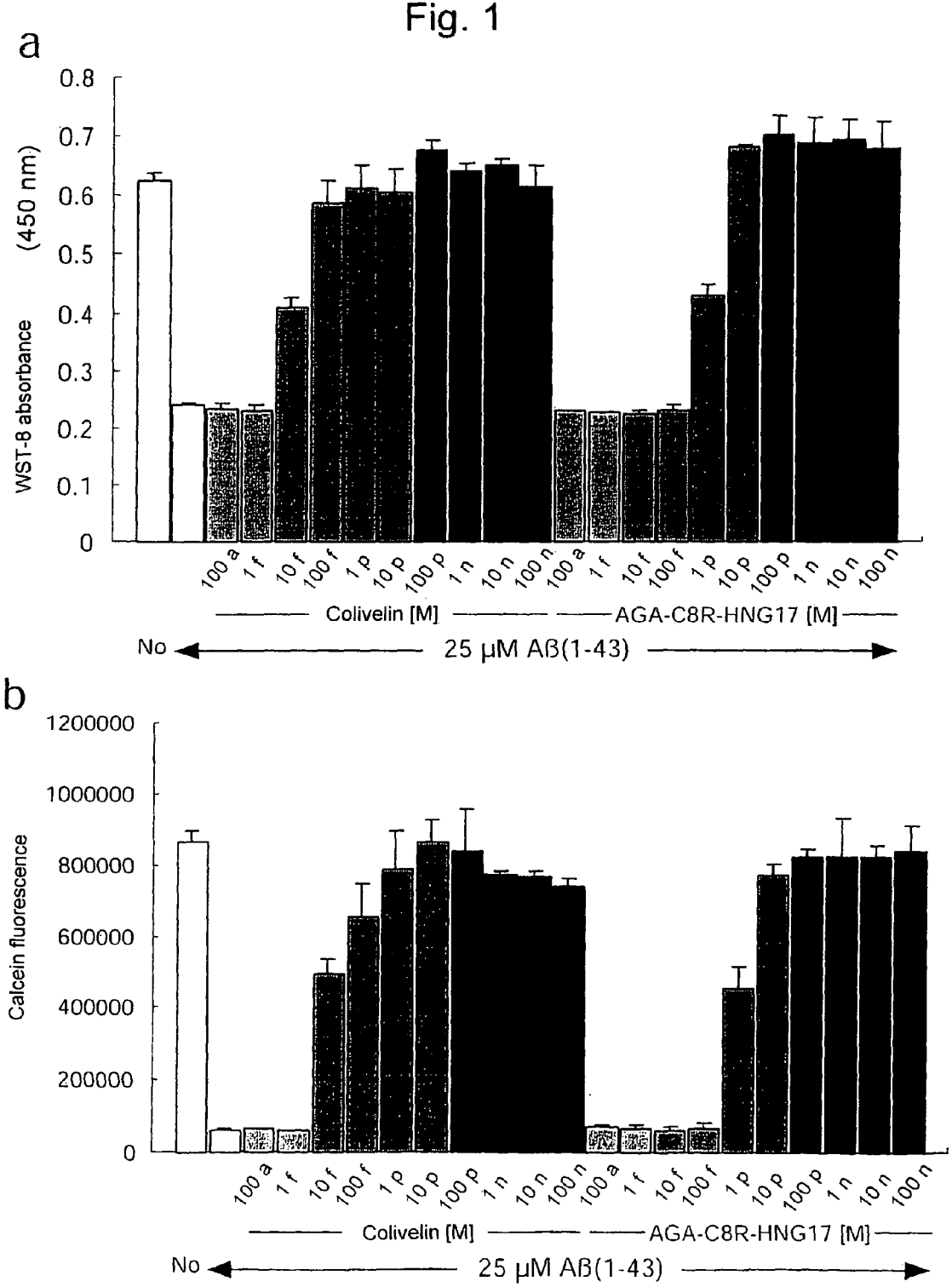
FIG. 1 shows the protective effect of colivelin or AGA-CBR-HNG17 on neuronal cell death of primary cortical neurons caused by Aβ (1-43), wherein the results of cell viability measured by WST-8 assay (FIG. 1a) and calcein cell viability assay (FIG. 1b) 72 hours after Aβ treatment are shown.

Hereinafter, the present invention will be described in detail. The present application claims the priority of U.S. Provisional Application No. 60/560,254 filed on Apr. 8, 2004 and encompasses contents as described in the specification and/or drawings of the priority application.

DETAILED DESCRIPTION OF THE INVENTION

Polypeptide

A polypeptide of the present invention is (a) a polypeptide comprising the amino acid sequence represented by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), a modified polypeptide thereof, or a salt thereof; or (b) a polypeptide comprising an amino acid sequence having a deletion, substitution, insertion, and/or addition of one or several amino acids in the amino acid sequence consisting of Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), and having an activity that inhibits neuronal cell death associated with neurodegenerative disease, a modified polypeptide thereof, or a salt thereof.

The polypeptide comprising the amino acid sequence represented by SEQ ID NO: 1 encompasses not only the polypeptide consisting of the amino acid sequence represented by SEQ ID NO: 1 but also a polypeptide comprising the amino acid sequence together with another amino acid sequence as long as it has an activity that inhibits neuronal cell death associated with neurodegenerative disease. Examples of another amino acid sequence include Val-Lys-Arg-Arg-Ala (SEQ ID NO: 7), Met-Ala, and derivatives with conservative amino acid substitutions thereof (Hashimoto, Y et al., 2001, J. Neurosci., 21: 9235-9245; and Terashita, K et al., 2003, J. Neurosci., 85: 1521-1538).

In the present invention, the polypeptide having an activity that inhibits neuronal cell death associated with neurodegenerative disease is a polypeptide having, as defined above, the activity of the polypeptides of the present invention as active agents to inhibit, antagonize, or suppress the neuronal cell death associated with neuronal degeneration and/or loss in neurodegenerative disease or the enhancement of neurotoxicity leading to the neuronal cell death. Such a polypeptide can inhibit, antagonize, or suppress the neuronal cell death induced, for example, by mutated superoxide dismutase-1 (SOD1) in amyotrophic lateral sclerosis (ALS), or for example, by mutated amyloid precursor protein (APP), mutated presenilin (PS)-1 or 2, or β-amyloid (Aβ) in Alzheimer's disease (AD), or for example, by mutations of polyglutamine repeat in HD, or the enhancement of neurotoxicity leading to the neuronal cell death.

The present invention also encompasses a mutant of the polypeptide consisting of the amino acid sequence of SEQ ID NO: 1. A preferable mutant is a polypeptide comprising an amino acid sequence having a deletion, substitution, insertion, and/or addition of one or several amino acids in the amino acid sequence consisting of SEQ ID NO: 1, and having an activity that inhibits neuronal cell death associated with neurodegenerative disease. Alternatively, another preferable mutant has 70% or higher, 75% or higher, 80% or higher, 85% or higher, 90% or higher, 95% or higher, or 97% or higher identity to the amino acid sequence consisting of SEQ ID NO: 1 and has an activity that inhibits neuronal cell death associated with neurodegenerative disease. The % identity between amino acid residues can be determined with search systems based on BLAST programs such as BLASTP (Altschul, S F et al., 1990, J. Mol. Biol., 215: 403-410).

The term "several" as used herein means, for example, 15 or less, 14 or less, 13 or less, 12 or less, or 11 or less, preferably 10 or less, 9 or less, 8 or less, 7 or less, or 6 or less, more preferably 5 or less, 4 or less, 3 or less, or 2 or less.

In the present invention, the amino acid sequence of SEQ ID NO: 1 may have a deletion, substitution, and/or addition (or insertion) of an amino acid(s) as long as the resulting polypeptide has an activity that inhibits neuronal cell death associated with neurodegenerative disease. For the deletion, it is preferred that the amino acid residues from 1-Ser to 15-Arg and the 21-Gly are not deleted in the amino acid sequence of SEQ ID NO: 1. For the addition, it is preferred that one or more amino acid residues, for example 1 to 10 amino acid residues, preferably 1 to 5 amino acid residues are added to the N terminus and/or C terminus of the amino acid sequence of SEQ ID NO: 1. For the substitution, the substitution of identical amino acids between L and D, or the substitution between conservative amino acids (i.e., conservative substitution), is preferable. The conservative substitution refers to the substitution between conservative amino acids in amino acid groups similar in electrical, hydrophobic, or structural property. The conservative amino acid groups can be divided into basic amino acids (e.g., lysine, arginine, and histidine), acidic amino acids (e.g., aspartic acid and glutamic acid), uncharged polar amino acids (e.g., glycine, asparagine, glutamine, serine, threonine, tyrosine, and cysteine), nonpolar amino acids (e.g., alanine, valine, leucine, isoleucine, proline, phenylalanine, methionine, and tryptophan), β-branched amino acids (e.g., threonine, valine, and isoleucine), and aromatic amino acids (e.g., tyrosine, phenylalanine, tryptophan, and histidine). In the present invention, the substation may be performed between amino acids in each of these groups.

According to an embodiment of the present invention, the polypeptide of the present invention comprises an amino acid sequence represented by the following formula: Ser-Ala-Leu-Leu-Arg-Ser-Ile-Pro-Ala-Pro-$Xn_1$-(Cys, Arg, Lys, or His)-(Leu or Arg)-$Xn_2$-Leu-Thr-(Gly, L-Ser, or D-Ser)-$Xn_3$-Pro (SEQ ID NO: 2), wherein $Xn_1$ comprises an amino acid sequence consisting of (Arg or Ala)-(Gly or Ala)-(Phe or Ala)-(Ser or Ala) (SEQ ID NO: 3), $Xn_2$ comprises an amino acid sequence consisting of (Leu or Ala)-(Leu or Ala), and $Xn_3$ comprises an amino acid sequence consisting of (Glu or Ala)-(Ile or Ala)-(Asp or Ala)-(Leu or Ala) (SEQ ID NO: 4).

Examples of the sequence $Xn_1$ include Arg-Gly-Ala-Ser (SEQ ID NO: 8), Arg-Gly-Phe-Ser (SEQ ID NO: 9), Ala-Gly-Phe-Ser (SEQ ID NO: 10), Arg-Ala-Phe-Ser (SEQ ID NO: 11), and Arg-Gly-Phe-Ala (SEQ ID NO: 12).

Examples of the sequence $Xn_2$ include Leu-Leu, Ala-Leu, Leu-Ala, and Ala-Ala.

Examples of the sequence of $Xn_3$ include Glu-Ile-Asp-Leu (SEQ ID NO: 13), Ala-Ile-Asp-Leu (SEQ ID NO: 14), Glu-Ala-Asp-Leu (SEQ ID NO: 15), Glu-Ile-Ala-Leu (SEQ ID NO: 16), and Glu-Ile-Asp-Ala (SEQ ID NO: 17).

According to another embodiment of the present invention, the polypeptide of the present invention is a polypeptide dimer. The dimerization requires, for example, the 14-Ser residue of the amino acid sequence of SEQ ID NO: 1. The dimerization enhances the activity that inhibits neuronal cell death.

According to a further embodiment of the present invention, the polypeptide of the present invention is a fusion with another peptide or polypeptide. The fusion may be produced by peptide synthesis or can also be produced by expressing DNA wherein the coding regions of the polypeptides are ligated in frame. Examples of the another peptide or polypeptide include, but not limited to, tags, leader sequences, signal peptides, green fluorescent proteins (GFP), maltose-binding proteins, glutathione S-transferase (GST), and antibody fragments.

The tag or GFP and the leader sequence or signal peptide are intended to facilitate polypeptide purification. The leader sequence or signal peptide helps extracellularly secrete the foreign polypeptide of the present invention, when the polypeptide is produced with genetically engineered host cells. In the present invention, any signal peptide of secretion proteins known in the art, which is selected depending on the types of host cells, can be used. Regarding the tag or GFP, the polypeptide of the present invention is generated in a form fused with the tag or GFP, when commercially available vectors (e.g., pHB6, pVB6, pBH, and pHM6 (all from Roche Diagnostics)) are used to express DNA encoding the polypeptide in bacterial hosts such as *Escherichia coli*. Any of tags known in the art can be used, and examples thereof include FLAG, 6×His, 10×His, influenza hemagglutinin (HA), VSV-GP fragments, T7-tag, HSV-tag, and E-tag. For example, a fusion of the polypeptide with His tag can be purified with metal (Ni or Co) affinity resin columns.

The polypeptide of the present invention also encompasses a salt thereof, that is, an acid-addition salt or base-addition salt. Examples of the acid-addition salt can include: salts of mineral acids such as hydrochloride, sulfate, nitrate, hydrobromide, and phosphate; and salts of organic acids such as acetate, butyrate, succinate, citrate, oxalate, malate, methanesulfonate, benzoate, maleate, and tartrate. Examples of the base-addition salts can include: alkali metal salts (e.g., sodium salts and potassium salts) and alkaline-earth metal salts (e.g., calcium salts and magnesium salts); and salts formed with organic bases such as ammonium salts (e.g., ammonium salts, methylammonium salts and triethylammonium salts) and amino acid salts (e.g., lysine salts and arginine salts).

Furthermore, the polypeptide of the present invention or the salt thereof can also exist as hydrates or solvates.

The polypeptide of the present invention may further be modified chemically or biologically. Examples of the modification can include, but not limited to, functional group introduction such as alkylation, acylation, amidation, esterification, halogenation, amination, carboxylation, and pegylation, functional group conversion such as oxidation, reduction, addition, and elimination, glycosylation, lipid compound introduction, phosphorylation, and biotinylation. Such modification may be performed, for example, for the purpose of stabilizing the polypeptide of the present invention, enhancing biological activity, sustaining pharmacological effect, suppressing antigenicity, etc.

The polypeptide of the present invention can be produced according to a peptide synthesis technique known in the art. Specifically, they can be synthesized by a variety of methods such as azide method, acid chloride method, acid anhydride method, mixed anhydride method, DCC method, activated ester method (e.g., P-nitrophenyl ester, N-hydroxysuccinimide ester, and cyanomethyl ester methods), methods using Woodward's reagent K, carboimidazole method, oxidation-reduction method, and DCC-additive (HONB, HOBt, or HOSu) method according to the descriptions of, for example, "The Peptides" Vol. 1 (1966) [Schroder and Lubke, Academic Press, New York, U.S.A.] or "Peptide Synthesis" [Izumiya et al., Maruzen Co., Ltd., (1975)]. These methods can be applied to both solid-phase and liquid-phase syntheses.

In the solid-phase method, a variety of commercially available peptide synthesizers can be utilized. The synthesis can be performed more efficiently by protecting and deprotecting functional groups, if necessary. For example, Protective Groups in Organic Synthesis (T. W. Greene, John Wiley & Sons Inc., 1981) can be referenced for procedures for introducing and eliminating protecting groups.

The obtained polypeptide can be desalted and purified according to a typical method. Examples thereof include ion-exchange chromatography such as DEAE-cellulose, partition chromatography such as Sephadex LH-20 and Sephadex G-25, normal phase chromatography such as silica gel, reverse phase chromatography such as ODS-silica gel, and high performance liquid chromatography.

2. Nucleic Acid

The present invention also provides DNA encoding any of the following polypeptides (a) to (c) of the present invention:

(a) a polypeptide comprising the amino acid sequence represented by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), or a fusion polypeptide with another peptide or polypeptide;

(b) a polypeptide comprising an amino acid sequence having a eletion, substitution, insertion, and/or addition of one or several amino acids in the amino acid sequence consisting of Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), and having an activity that inhibits neuronal cell death associated with neurodegenerative disease, or a fusion polypeptide with another peptide or polypeptide; and (c) a polypeptide comprising an amino acid sequence represented by Ser-Ala-Leu-Leu-Arg-Ser-Ile-Pro-Ala-Pro-$Xn_1$-(Cys, Arg, Lys, or H is)-(Leu or Arg)-$Xn_2$-Leu-Thr-(Gly, L-Ser, or D-Ser)-$Xn_3$-Pro, (SEQ ID NO: 2) wherein $Xn_1$ comprises an amino acid sequence consisting of (Arg or Ala)-(Gly or Ala)-(Phe or Ala)-(Ser or Ala), $Xn_2$ comprises an amino acid sequence consisting of (Leu or Ala)-(Leu or Ala), and $Xn_3$ comprises an amino acid sequence consisting of (Glu or Ala)-(Ile or Ala)-(Asp or Ala)-(Leu or Ala), or a fusion polypeptide with another peptide or polypeptide.

The DNA of the present invention also encompasses a mutant having 70% or higher, 75% or higher, 80% or higher, 85% or higher, 90% or higher, 95% or higher, 97% or higher, 98% or higher, or 99% or higher identity to a nucleotide sequence encoded by the polypeptide of SEQ ID NO: 1. The % identity between bases can be determined with BLAST programs such as BLASTN and BLASTX known in the art (Altschul, S F et al., 1990, J. Mol. Biol., 215: 403-410).

The DNA of the present invention can be used for producing the polypeptide of the present invention by use of a gene recombination technique or for producing the polypeptide of the present invention in vivo to treat a subject.

When the polypeptide of the present invention is produced by use of a gene recombination technique, a recombinant vector comprising the DNA encoding the polypeptide of the present invention is produced, and a prokaryotic or eukaryotic host cell transformed with the vector is prepared and cultured. The polypeptide of the present invention can be separated and purified from the resulting host cell or culture supernatant thereof.

In the polypeptide production by the gene recombination technique, the polypeptide can be secreted actively outside of the host cell by expressing it in the form of fusion polypeptide with a signal peptide for extracellular secretion added to the N terminus thereof. Furthermore, a tag for purification/detection can be added to between the signal peptide and the polypeptide or to the C terminus of the oligopeptide.

To produce the fusion polypeptide, the DNA encoding the polypeptide of the present invention and DNA encoding another peptide or polypeptide may be ligated in frame and introduced into an expression vector to express the fusion protein in a host cell.

A signal peptide of any secretion protein known in the art, which is selected depending on the types of host cells, can be used as the signal peptide of the present invention. When animal cells are used as host cells, examples of the signal peptide include signal peptides present in the N termini of growth and differentiation factors (e.g., a variety of cytokines) and receptors thereof.

Any of tags known in the art can be used as the tag for purification/detection, and examples thereof include FLAG, 6×His, 10×His, influenza hemagglutinin (HA), VSV-GP fragments, T7-tag, HSV-tag, and E-tag.

Vectors for prokaryotic and eukaryotic cells (e.g., *Escherichia coli, Bacillus subtilis*, yeast, *Basidiomycetes*, insect cells, plant cells, and mammalian cells) can be used in a host-vector system for expressing the DNA encoding the polypeptide of the present invention. Examples of such vectors include plasmid, phage, and virus vectors. The vector into which the DNA of the present invention is inserted is not particularly limited as long as it is capable of replication in hosts. Examples of the vector include plasmids such as plasmids for *Escherichia coli*, plasmids for *Bacillus subtilis*, plasmids for yeast, and plasmids for mammal cells and phages such as λ phages. Furthermore, animal viruses such as retrovirus or vaccinia virus and insect viral vectors such as baculovirus can also be used. These vectors are commercially available, and in the present invention, such commercially available vectors can be used. Examples thereof include pQE (Qiagen), pBluescript, pNH (Stratagene), and pKK (Pharmacia) series of vectors. Alternatively, examples of therapeutic vectors include adenovirus vectors, adeno-associated virus vectors, herpes virus vectors, retrovirus vectors, and lentivirus vectors (Robbins and Ghivizzani, 1998, Pharmacol. Ther., 80: 35-37; Engel and Kohn, 1999, Front Biosci., 4: e26-33; and Lundstrom, K, 1999, J. Recept. Signal. Transduct. Res., 19: 673-686).

To insert DNA of the present invention into a vector, a method which initially cleaves the purified DNA with appropriate restriction enzymes and inserts and ligates it to the restriction site or multicloning site of appropriate vector DNA is adopted.

The DNA encoding the polypeptide of the present invention must be incorporated into the vector so that the function of the DNA is exerted. Thus, the vector of the present invention can be ligated with cis elements (e.g., promoters and enhancers), splicing signals, polyA-addition signals, selective markers, ribosome-binding sequences (SD sequences), terminators, and so on. Examples of the promoters include LacI, LacZ, PL, and Trp promoters as promoters for bacteria and SV40, HSV thymidine kinase, mouse metallothionein, retrovirus-derived LTR promoters as eukaryotic cell promoters. Examples of the selective markers include dihydrofolate reductase genes, ampicillin resistance genes, neomycin resistance genes, and kanamycin resistance genes.

The vector of the present invention is introduced into host cells so that the DNA of the present invention can be expressed. The host cells are not particularly limited, and examples thereof include: bacteria belonging to the genus *Escherichia* such as *Escherichia coli* and the genus *Bacillus* such as *Bacillus subtilis*; yeasts such as *Saccharomyces cerevisiae* and *Schizosaccharomyces pombe*; animal cells such as monkey COS-7 cells, Vero, Chinese hamster ovary cells (CHO cells), mouse L cells, human GH3 cells, and human FL cells; and dicotyledonous or monocotyledonous cells (e.g., tobacco).

Examples of methods for introducing the recombinant vector into the host cells include electroporation, calcium phosphate, lithium acetate, lipofection, virus, and *Agrobacterium* methods, which are selected depending on the types of host cells. Methods independent of recombinant vectors, for example particle gun method, can also be used for gene delivery to each of the host cells.

The polypeptide of the present invention can be obtained from a culture obtained by culturing the host cell of the present invention in an appropriate culture medium. The "culture" means any of culture supernatants, cultured cells or cultured microorganisms, and homogenates of the cells or microorganisms.

The host cell of the present invention can be cultured according to a method typically used for culturing the host cell.

Both natural and synthetic media may be used as the medium for culturing host cells from a microorganism such as *Escherichia coli* or yeast used as a host as long as the media contain carbon sources, nitrogen sources, inorganic salts, and so on capable of being assimilated by the microorganism and can achieve the efficient culture of the transformant. The carbon sources may be those capable of being assimilated by the microorganism. Carbohydrates such as glucose, fructose, sucrose, and starch, organic acids such as acetic acid and propionic acid, and alcohols such as ethanol and propanol can be used. Ammonium salts of inorganic or organic acids (e.g., ammonia, ammonium chloride, ammonium sulfate, ammonium acetate, and ammonium phosphate), other nitrogen-containing compounds, peptone, meat extracts, corn steep liquor, and so on can be used as the nitrogen sources. Monopotassium phosphate, dipotassium phosphate, magnesium phosphate, magnesium sulfate, sodium chloride, ferrous sulfate, manganese sulfate, copper sulfate, calcium carbonate, and so on can be used as the inorganic salts.

When the polypeptide of the present invention is produced into the microorganisms or cells after culture, the polypeptide is extracted by homogenizing the microorganism or cells. When the polypeptide is produced outside of the microorganism or cells, the culture liquid is directly used or, for example, centrifuged to remove the microorganism or cells. Then, the polypeptide of the present invention can be isolated and purified from the culture by using, alone or in appropriate combination, general biochemical methods used in protein isolation and purification, for example ammonium sulfate precipitation, gel chromatography, ion-exchange chromatography, and affinity chromatography.

3. Pharmaceutical Composition

The present invention further provides a pharmaceutical composition for the treatment and/or prevention of a neurodegenerative disease comprising the polypeptide or vector of the present invention.

As demonstrated in Examples (mouse experiments) below, the polypeptide of the present invention has neuroprotective action on neurodegenerative disease because the polypeptide suppressed the neuronal cell death induced by mutant (G93R) SOD1 (an ALS model) or the neuronal cell death induced by mutant (M146L) PS-1 or Aβ (1-43 or 25-35) (an AD model).

The polypeptide of the present invention, particularly the polypeptide consisting of the amino acid sequence represented by SEQ ID NO: 1 (i.e., colivelin), has a fusion sequence of ADNF (SEQ ID NO: 5) and AGA-C8R-HNG17 (SEQ ID NO: 6) sequences.

Although ADNF has a neuroprotective effect on neuronal cell death induced by SOD1 mutant (e.g. A4T-SOD1, G85R-SOD1, and G93R-SOD1) (an ALS model), and a neuroprotective effect on neuronal cell death induced by Aβ toxicity (an AD model), its protective effect on Aβ toxicity is drastically reduced at a dose equal to or above approximately 1 nM. Moreover, the life span-prolonging effect of ADNF is small.

AGA-C8R-HNG17 protected neurons from neuronal cell death induced by mutant (M146L) PS-1 or Aβ (1-43) (an AD model) and however, could not protect neurons from neuronal cell death induced by SOD1 mutant (an ALS model).

By contrast, the colivelin of the present invention at a dose of equal to or above 10 fM, particularly 100 fM or more, exhibited a more potent neuroprotective effect than those of ADNF and AGA-C8R-HNG17 on both ALS and AD models. Its protective effect was not reduced even at a dose of 100 nM. Moreover, the colivelin of the present invention provides life span-prolonging effect and the effect of recovering approximately 70% of motor function in experiments using ALS model mice.

Based on the findings, it is found that the colivelin-containing polypeptide of the present invention is effective as a therapeutic drug for neurodegenerative disease caused by neuronal cell death associated with neuronal degeneration and/or loss. Therefore, the polypeptide of the present invention has an activity that inhibits neuronal cell death, that is, the activity to inhibit, antagonize, or suppress neuronal cell death associated with neuronal degeneration and/or loss in neurodegenerative disease or the enhancement of neurotoxicity leading to the neuronal cell death.

Examples of the neurodegenerative diseases to be treated by the present invention include, but not limited to, cerebral degenerative diseases (e.g., AD, Parkinson's disease, progressive supranuclear palsy, and Huntington's disease (HD)) and spinal degenerative diseases/motor neuron degenerative diseases (e.g., ALS, spinal muscular atrophy (SMA: Werdnig-Hoffmann disease or Kugelberg-Welander syndrome), spinocerebellar ataxia, bulbospinal muscular atrophy (BSMA: Kennedy-Alter-Sung syndrome)). As used herein, the "motor neuron degenerative disease" refers to a neurodegenerative disease with a progressive, retrograde disorder of upper and lower motor neurons that control motion in the body.

Neuronal cell death is induced, for example, by SOD1 mutant in ALS, or for example, by mutant APP, PS-1, or PS-22, or Aβ in AD, or for example, by polyglutamine repeat mutations in HD.

The pharmaceutical composition of the present invention can be used as a preventive agent preventing or delaying the onset of the neurodegenerative diseases and/or a therapeutic agent allowing the diseases to recover to the normal state or alleviating or suppressing the conditions of the diseases.

The pharmaceutical composition of the present invention is also effective for the amelioration of conditions resulting from the motor neuron degenerative disease. The amelioration of conditions refers to the improvement of, for example, muscular atrophy, muscular weakness, bulbar palsy (muscular atrophy or weakness in the face, pharynx, and tongue, and aphasia or dysphagia caused thereby), muscular fasciculation, and respiratory disorder.

The pharmaceutical composition of the present invention can be prepared into various types of dosage forms by a variety of methods generally known in pharmaceutical industries, and provided as a medicament.

The pharmaceutical composition of the present invention, when orally administered, may be prepared into tablets, capsules, granules, powders, pills, liquors for internal use, suspensions, solutions, emulsions, syrups, or the like, or may be made into dry forms that can be reconstituted for use. Alternatively, the pharmaceutical composition of the present invention, when parenterally administered, is prepared into injections such as intravenous injections (including infusion), intramuscular injections, intraperitoneal injections, and subcutaneous injections, or into suppositories, and the preparation for injection is provided in the form of unit dosage ampule or multiple dosage container. Furthermore, it may be made into a preparation capable of passing through the blood-brain barrier or may be made into a preparation that can be administered spinally or intracerebroventricularly.

Various types of these preparations can be produced by a routine method by appropriately selecting pharmaceutically acceptable excipients, fillers, binders, wetting agents, disintegrants, lubricants, surfactants, dispersants, buffers, preservatives, solubilizers, antiseptics, flavors, soothing agents, stabilizers, tonicity agents, and so on. The content of the polypeptide of the present invention serving as an effective ingredient in the pharmaceutical composition is, but not limited to, for example approximately 0.001 to approximately 10% by weight. The concentration of the active ingredient in the composition is, but not limited to, for example approximately 100 fM or higher, approximately 1 pM or higher, approximately 1 nM or higher, approximately 10 nM or higher, approximately 100 nM or higher, or approximately 1 μM or higher.

When the pharmaceutical composition of the present invention is used as a preventive and/or therapeutic agent for the diseases described above, it can be administered parenterally or orally to mammals such as humans, mice, rats, rabbits, dogs, and cats. The dose and number of doses of the pharmaceutical drug of the present invention may be changed appropriately according to the age, sex, and conditions of a subject to be administered, or administration routes. For example, the dose of an effective amount of the polypeptide of the present invention combined with suitable diluents and pharmacologically available carriers is, but not limited to, for example in the range of approximately 1 to approximately 500 µg/kg of body weight/day.

The active ingredient of the pharmaceutical composition of the present invention may be DNA encoding the polypeptide of the present invention. When the DNA encoding the oligopeptide is used as a gene therapy agent for the disease described above, examples of administration methods thereof include a method which administers a vector incorporating the DNA therein. Examples of the vector include plasmids, adenovirus vectors, adeno-associated virus vectors, herpes virus vectors, vaccinia virus vectors, and retrovirus vectors. The therapeutic agent can be expressed in vivo with efficiency by infecting organisms with the viral vectors. Alternatively, a method which introduces the vector or the DNA into liposomes (e.g., positively charged liposomes and positively charged cholesterol) and administers the liposome can be used as an effective therapy.

The administration mode of the gene therapy agent may be any of local administration such as administration to muscle (e.g., quadriceps femoris muscle or gluteus maximus), cerebral ventricle, and spinal cord, and systemic administration such as typical intravenous or intraarterial administration, and is preferably local administration. Furthermore, the administration mode combined with catheter techniques, surgical operation, and so on, can be adopted.

BEST MODE FOR CARRYING OUT THE INVENTION

Hereinafter, the present invention will be described more fully with reference to Examples. However, the present invention is not intended to be limited by these Examples.

All of experiments using neuronal cell lines described in Examples below were repeated at least three times with independent transformations and treatments, each of which gave essentially the same results. Statistical analysis was conducted by one-way ANOVA, followed by a Bonferroni/Dunn post-hoc test, in which $p<0.05$ was assessed as being significant.

Animal experiments were conducted according to Policies on the Use of Animals and Humans in Neuroscience Research, the Society for Neuroscience and Guideline for Care and Use of Laboratory Animals of KEIO University in Japan. All experimental procedures were approved by Institutional Animal Experiment Committee at KEIO University in Japan.

Example 1

Protective Effect of Colivelin on Neuronal Cell Death Induced by a Variety of Factors (1) Test Materials M146L-PS1 cDNA incorporated in pcDNA vector has been reported previously (Hashimoto Y, et al., 2001, J Neurosci 21: 9235-9245).

SOD1 mutant (G93R-SOD1) cDNA was kindly provided by Dr. Shoji Tsuji (Faculty of Medicine, the University of Tokyo, Japan).

Colivelin: ADNF-AGA-CBR-HNG17 (SALLRSIPA-PAGASRLLLLTGEIDLP: SEQ ID NO: 1), AGA-C8R-HNG17 (PAGASRLLLLTGEIDLP: SEQ ID NO: 6), and ADNF (SALLRSIPA: SEQ ID NO: 5) were synthesized (Glazner G W, et al., 1999, J Neurochem 73: 2341-2347).

An anti-SOD1 antibody was purchased from MBL (Nagoya, Japan).

F11 cell, the hybrid cell of rat embryonic day 13 (E13) primary cultured neuronal cell with mouse neuroblastoma NTG18 cell, was cultured in Ham's F-12 medium (Life Technologies, Gaithersburg, Md.) containing 18% FBS (Hyclone, Logan, Utah) and antibiotics as previously reported (Platika D, et al., 1985, Proc Natl Acad Sci USA 82: 3499-3503; Yamatsuji T, et al., 1996, Science 272: 1349-1352; Huang P, et al., 2000, Mol Hum Reprod 6: 1069-1078; and Niikura T, et al., 2001, J Neuroscience, 21: 1902-1910).

NSC34 cell, the hybrid cell of primary cultured, motor neuron-system embryonic mouse spinal cord cell with mouse neuroblastoma NTG18 cell, was cultured in DEME medium containing 10% FBS and antibiotics (Cashman N R, et al., 1992, Dev Dyn 194: 209-221; and Durham H D, et al, 1993, Neurotoxicology 14: 387-395).

(2) Test Method (2-1) Neuronal Cell Death Test (i) Test of Neuronal Cell Death Induced by M146L-PS1 or G93R-SOD1 Gene The F11 cells ($7\times10^4$ cells/well, 6-well plate, 12- to 16-hour culture in Ham's F-12 (18% FBS) medium) were transformed with M146L-PS1 or G93R-SOD1 gene by lipofection (0.5 µg of cDNA; 1 µl of LipofectAMINE; 2 µl of PLUS Reagent) under serum-free conditions for 3 hours and cultured for 2 hours in Ham's F-12 (18% FBS) medium. The medium was replaced by Ham's F-12 (10% FBS) in the presence or absence of varying concentrations (100 aM, 1 fM, 10 fM, 100 fM, 1 pM, 10 pM, 100 pM, 1 nM, 10 nM, or 100 nM) of colivelin or AGA-CBR-HNG17 peptides. After 72 hours of the transformation, cell mortality was measured by Trypan blue exclusion assay as previously reported (Hashimoto Y, et al., 2001, J Neurosci 21: 9235-9245; and Hashimoto Y, et al, 2001, Proc Natl Acad Sci USA 98: 6336-6341).

(ii) Test of Neuronal Cell Death Induced by Aβ (1-43) Peptide

Mouse cortical neurons were primarily cultured on a poly-D-lysine-coated 96-well plate (Sumitomo Bakelite, Akita, Japan) in the absence of serum and the presence of N2 supernatant according to the previous report (Sudo et al., 2000, Mol. Cell. Neurosci., 16: 708-723). The purity of the neurons by this method was 98% or more. The prepared neurons ($5.0\times10^4$ cells/well, 100 µl of medium/well) were cultured for 72 hours in the presence or absence of varying concentrations (100 aM, 1 fM, 10 fM, 100 fM, 1 pM, 10 pM, 100 pM, 1 nM, 10 nM, or 100 nM) of colivelin or AGA-C8R-HNG17 peptide. Since primary cultured neurons temporarily become fragile during medium replacement, the neurons were treated with 25 µM Aβ as follows: at first, a half volume (50 µl) of the old medium was discarded. Next, 50 µM Aβ and 50 µl of prewarmed fresh medium containing varying concentrations of colivelin or AGA-CBR-HNG17 peptides were added to the culture. Aβ (1-43) was purchased from Peptide Institute. The Aβ peptides used at the concentration of 25 µM for inducing neuronal cell death formed aggregation in the medium during 72-hour cell culture at 37° C. (Hashimoto Y, et al., 2001, J Neurosci 21: 9235-9245).

WST-8 cell viability assay was conducted with Cell Counting Kit-8 according to the previous report (Hashimoto Y, et al, 2001, Proc Natl Acad Sci USA 98: 6336-6341).

Calcein assay was conducted with calcein-AM (Dojindo, Kumamoto, Japan) according to the previous report (Hashimoto Y, et al., 2001, J Neurosci 21: 9235-9245).

These assays were simultaneously performed. After 72 hours of the Aβ treatment, the cells were added to a mixture of 10 μl of WST-8 solution and 1 μl of 600 μM calcein-AM and cultured at 37° C. for 2 hours in a $CO_2$ incubator to measure a WST-8 absorption at O.D. 450. To decrease background, the medium was replaced by phosphate-buffered saline, followed by the measurement of calcein-specific fluorescence (excitation: 485 nm, emission: 535 nm) by fluorescence microcopy or with a spectrofluorometer (Wallac 1420 ARVOsx Multi Label Counter; Perkin Elmer, Wellesley, Mass., USA).

(2-2) Immunoblot Analysis

Immunoblot analysis was conducted according to the previous report (Hashimoto Y, et al., supra, p. 6336-6341). To examine the protein expression of wild-type or SOD1 mutant genes, lysates from the cells transfected with each SOD1 gene were subjected to SDS-PAGE (20 μg/lane). After electroblotting to a PVDF membrane, the membrane was blocked by a typical method and reacted with an anti-SOD 1 antibody and then with a 1:5000-diluted horseradish peroxidase-conjugated anti-mouse IgG antibody (Bio-Rad Lab. Hercules, Calif., USA). The antibody-reactive bands were detected by ECL (Amersham Pharmacia Biotech, Uppsala, Sweden).

(3) Result (3-1) Protection by Colivelin or AGA-C8R-HNG17 Peptide Against Aβ (1-43)-Induced Neuronal Cell Death As reported previously, 10 nM Aβ (1-43) causes massive neuronal cell death (Yankner et al., 1990, Science, 250: 279-282; Loo et al., 1993, Proc. Natl. Acad. Sci. USA, 90: 7951-7955; Pike et al., 1993, J. Neurosci., 13: 1676-1687; Gschwind and Huber, 1995, J. Neurochem., 65: 292-300; Kaneko et al., 1995, J. Neurochem., 65: 2585-2593; Giovanni et al., 1999, J. Biol. Chem., 274: 19011-19016; and Sudo et al., 2001, BBRC, 282: 548-556). The protective effects of HN and S14G HN(HNG) against neurotoxicity by Aβ (1-43), which has been believed to be one of causes of AD (Alzheimer's disease) onset have been confirmed (Hashimoto Y, et al., 2001, J Neurosci 21:9235-9245; and Mann et al., 1996, Am J. Pathol., 148: 1257-1266). ADNF was originally purified from the primary culture of astrocytes and has been shown to have a neuroprotective action on some Alzheimer's disease-associated disorders including amyloid β peptides in Alzheimer's disease.

When primary cultured cortical neurons were treated with 25 μM Aβ (1-43), the cell viability was remarkably decreased within 72 hours as compared with that of the untreated control cells (FIG. 1a). When neurons were treated with 25 μM Aβ (1-43) in the presence of 10 fM colivelin or 1 pM AGA-C8R-HNG17, half of the neurons were rescued. Complete protection was achieved by 100 fM colivelin or 10 pM AGA-C8R-HNG17. This result showed that colivelin is 100-fold more potent than AGA-C8R-HNG17. Considering the fact that S14G-HN(HNG) exerts complete protective action at a concentration of 10 nM, colivelin can be said to be 100,000-fold more potent than HNG. ADNF at 100 fM completely protected the neurons from cell death induced by Aβ (1-43), and its protective activity attenuated at or over 1 nM. Colivelin is as potent as ADNF, and its protective activity did not disappear even at 100 nM. This showed that colivelin acts at low concentrations, as with ADNF, and works like HNG at high concentrations. Cell viability assay using calcein was conducted to verify these observations (FIG. 1b).

(3-2) Protective Action of Colivelin on M146L-PS1-Induced Neuronal Cell Death

As already reported, 100 nM HNG completely suppresses cell death caused by M146L-PS1, while ADNF does not suppress cell death caused by M146L-PS1 (Hashimoto, Y et al., 2001, Proc Natl Acad Sci USA, 98: 6336-6341 and 98: 12854; and Hashimoto, Y et al., 2001, J. Neurosci., 21: 9235-9245). To clarify the effect of colivelin against neurotoxicity caused by mutant PS1, the effect of colivelin on F11 neuronal cells transformed with M146L-PS1 was compared with that of AGA-C8R-HNG17. After 72 hours of the transformation, cell mortality was measured by Trypan blue exclusion assay.

Figure 2:
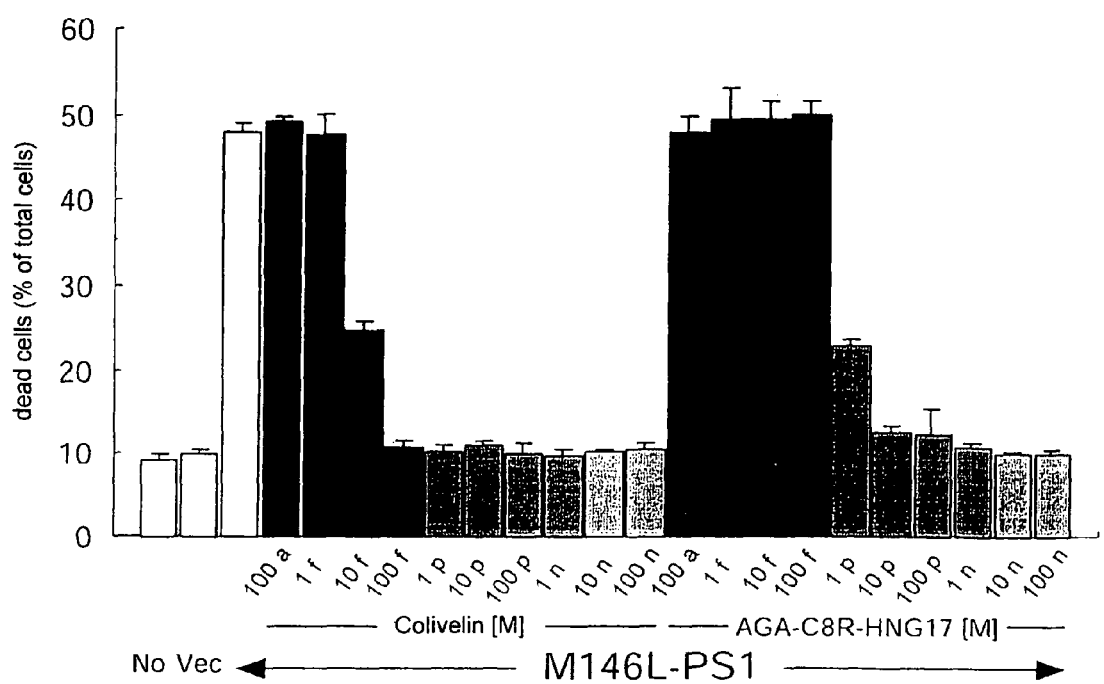
FIG. 2 shows the protective effect of colivelin or AGA-CBR-HNG17 on the neuronal cell death of F11 cells caused by transformation with M146L-PS1, wherein the results of the cell mortality of the F11 cells measured by Trypan blue exclusion assay 72 hours after transformation are shown.

Approximately 50% of the neurons died after the transformation with mutant PS I genes, whereas only 10% of the untreated or empty vector-transformed cells died. When the neurons transformed with the mutant genes were treated with 100 fM colivelin, the neurons died at a rate equal to that of the untreated or empty vector-transformed cells (FIG. 2). This showed that 100 fM colivelin completely suppresses cell death induced by mutant PS1. On the other hand, AGA-C8R-HNG17 exhibited its complete protection at 10 pM. Considering the fact that ADNF does not suppress neuronal cell death caused by PS1 mutations, it was suggested that colivelin exhibits its protective activity via the AGA-C8R-HNG17 domain, and that the protective activity of the AGA-C8R-HNG17 domain on PS1 mutations is enhanced by the ADNF domain.

(3-3) Protection by Colivelin Against G93R-SOD1-Induced Neuronal Cell Death

Figure 3:
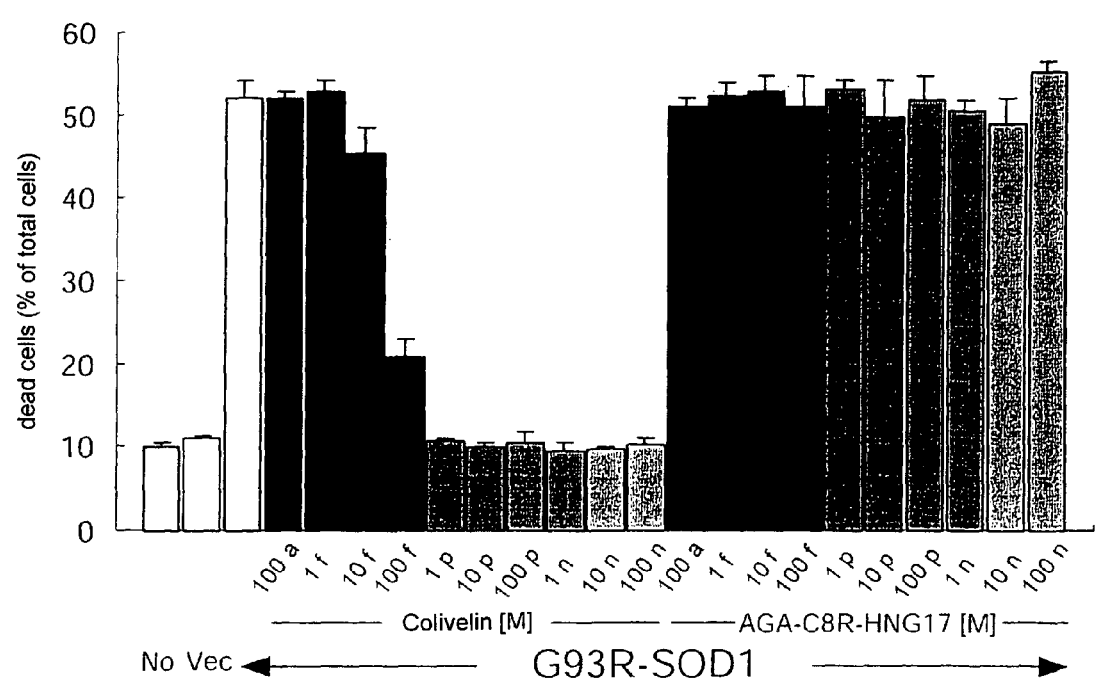
FIG. 3 shows the protective effect of colivelin or AGA-CBR-HNG17 on the neuronal cell death of F11 cells caused by transformation with G93R-SOD1, wherein the results of the cell mortality of the F11 cells measured by Trypan blue exclusion assay 72 hours after transformation is shown.

ADNF has already been reported to protect neurons from toxicity caused by SOD1 mutations. To clarify the effect of colivelin against neurotoxicity caused by SOD1 mutant, the effect of colivelin on neuronal cells transformed with G93R-SOD1 was compared with that of AGA-CBR-HNG17 (which has been found to antagonize neuronal cell death induced in some Alzheimer's disease-associated studies but fail to antagonize neuronal cell death induced by SOD1 mutants; Hashimoto Y, et al., supra). F11 cells were transformed with G93R-SOD1 gene to examine the influence of varying concentrations (100 aM, 1 fM, 10 fM, 100 fM, 1 pM, 10 pM, 100 pM, 1 nM, 10 nM, or 100 nM) of colivelin or AGA-C8R-HNG17 thereon. After 72 hours of the transformation, cell mortality was measured by Trypan blue exclusion assay (FIG. 3).

Approximately 50% of the F11 neuronal cells died after the transformation with G93R-SOD1 gene, whereas only 10% of the untreated or empty vector-transformed cells died. When the neurons transformed with G93R-SOD1 were treated with 1 pM colivelin, the neuronal cells died at a rate equal to that of the untreated or empty vector-transformed cells. This showed that 1 pM colivelin completely suppresses cell death induced by G93R-SOD1 genes. The F11 neuronal cells transformed with G93R-SOD1 were treated with varying concentrations of AGA-C8R-HNG17 to examine its effect thereon. However, its neuroprotective effect on cell death was not observed.

The data described above showed that colivelin exhibits its protective activity via the ADNF domain, and that the AGA-C8R-HNG17 domain had almost no influence on G93R-SOD1-induced cell death.

Example 2

Relationship of Neuroprotective Activity of Colivelin Against M146L-PS1-Induced Neuronal Cell Death, with Dimerization of its ADNF Domain The protective effect of colivelin and ADNF used together against neuronal cell death induced by M146L-PS1 was examined. F11 cells were transformed with M146L-PS1 in the presence or absence of 10 nM ADNF and treated with varying concentrations (100 aM, 1 fM, 10 fM, 100 fM, 1 pM, 10 pM, 100 pM, 1 nM, 10 nM, or 100 nM) of colivelin or AGA-C8R-HNG17.

Figure 4:
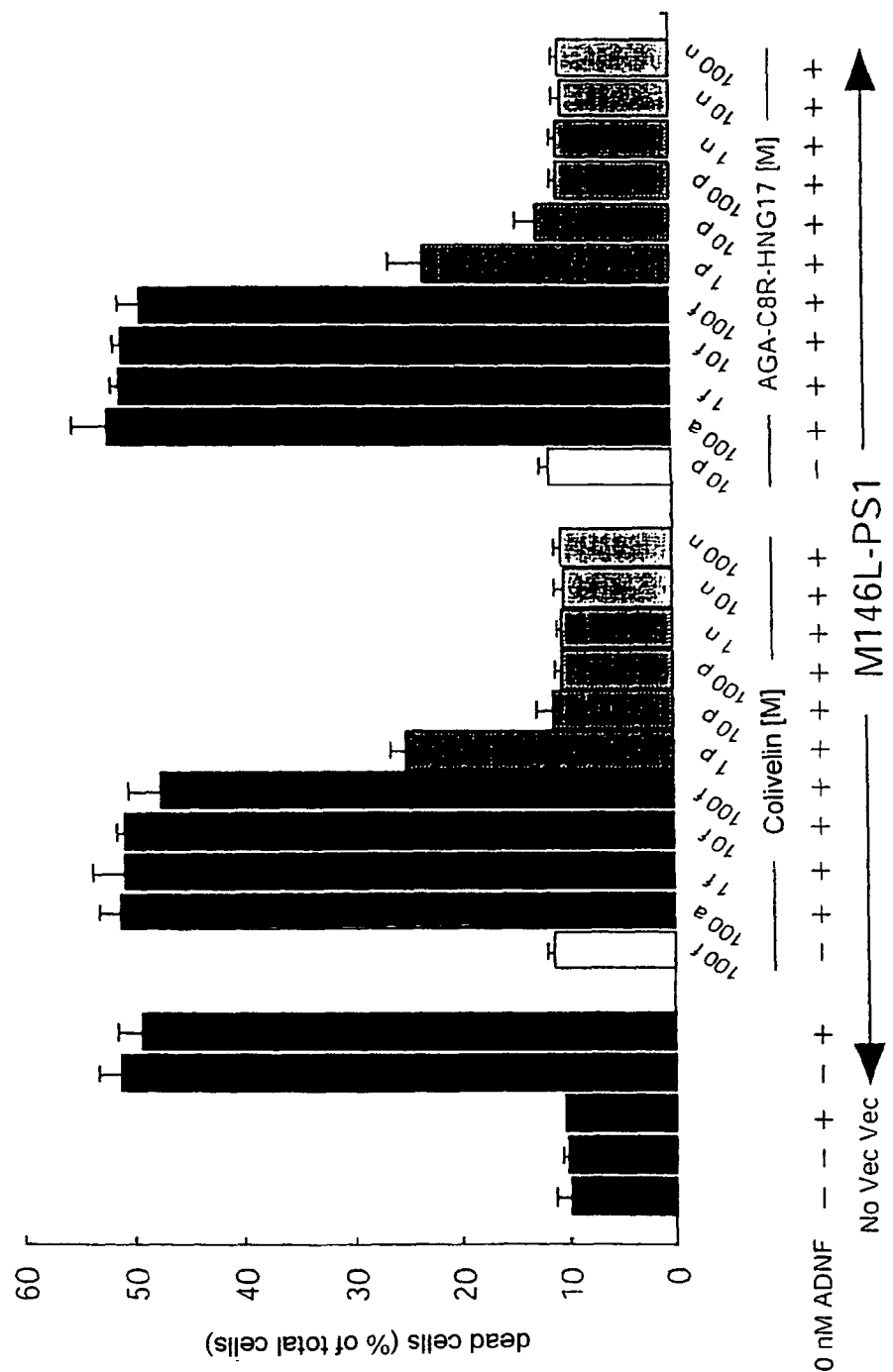
FIG. 4 shows that ADNF weakens the protective effect of colivelin on the neuronal cell death of F11 cells caused by transformation with M146L-PS1, wherein the results of the cell mortality of the F11 cells measured by Trypan blue exclusion assay 72 hours after transformation are shown in contrast with the protective effect of AGA-CBR-HNG17.

After 72 hours of the transformation, cell mortality was measured by Trypan blue exclusion assay (FIG. 4). Approximately 50% of the neuronal cells died after the transformation with mutant PS1 gene, whereas only 10% of the untreated or empty vector-transformed cells died. Neither general cell death nor M146L-PS1-induced neuronal cell death was affected by 100 nM ADNF itself. When the M146L-PS1-transformed neuronal cells in the presence of 100 nM ADNF were treated with 10 pM colivelin, the neuronal cells died at a rate equal to that of the untreated (No) or empty vector (vec)-transformed cells. This showed that colivelin at 10 pM, though this level is 1/100 of that without the combined use with 100 nM ADNF treatment, completely suppressed cell death induced by M146L-PS1 gene. By contrast, AGA-C8R-HNG17 alone exhibited its complete protective action at 10 pM, which was comparable to that without the 100 nM ADNF treatment or with the 100 nM ADNF+colivelin treatment.

The data described above showed that 100 nM ADNF competitively antagonized the dimerization of colivelin via the ADNF domain, and that its neuroprotective action became equal in level to that of AGA-C8R-HNG17.

Example 3

Motor Performance Test with ALS Model Animal (1) Animal Used

Transgenic (Tg) mice (hereinafter, referred to as "G93A-SOD1 Tg mice") expressing human FALS-associated SOD1 mutant gene with a mutation (G93A) from Gly to Ala at 93 position are the best-established mouse model of ALS (Gurney M E, et al., 1994, Science 264: 1772-1775; and Gurney M E, et al., 1997, J Neurol Sci 152 Suppl 1: S67-73). The G93A-SOD1 Tg mice manifest symptoms quite similar to human ALS after normal birth and rapidly result in death in all cases. The G93A-SOD1 Tg mice, which have the onset of the regression of motor neurons similar clinically and pathologically to that in human ALS, have been known so far to be the most excellent model of ALS throughout the world and employed for identifying effective candidate drugs for ALS patients.

(2) Test Methods

The model mice were used to confirm the in vivo effect of colivelin against neurotoxicity caused by G93A-SOD1.

The G93A-SOD1 Tg mice were purchased from Jackson Laboratories (Bar Harbor, Me.). The G93A-SOD1 Tg mice were kept as hemizygote mice by the mating thereof with C57BL/6J mice (CLEA Japan, Inc). The mice were raised in an SPF room (specific pathogen-free animal facility; 23±1° C., 55±5% humidity) in the 12-hour light/12-hour dark cycle (7:00 AM-7:00 PM). The mice were freely fed with gamma ray-irradiated Picolab Rodent Diet 20 (PMI Feeds Inc. St. Louis, Mo.) and sodium hyposulfite (5 ppm)-containing aseptic deionized distilled water.

The G93A-SOD1 Tg mice at 10 weeks of age were put under anesthesia by the intraperitoneal injection of 10% Nembutal (sodium pentobarbital; 60 mg/kg). A hole was made on the cranial bone with a drill on a sterotaxic surgery apparatus to aseptically transplant the C315GS-4 cannula system for mouse (Plastics One Inc., Roanoke, Va.) to the mouse left lateral ventricle. The cannula was fixed with a surgical adhesive and dental cement.

The mice at 80 days of age were divided at random to a saline (control)-administered group (n=7), 100 fmol colivelin-administered group (n=6), 10 pmol colivelin-administered group (n=7), 1 nmol colivelin-administered group (n=7), and 30 nmol ADNF-administered group (n=5). Until the end of the experiment, the control group received the intracerebroventricular (icv) injection of 3 µl of saline each day, while the colivelin-administered groups and the ADNF-administered group received the icv injection of 3 µl of colivelin (100 f mol, 10 pmol, or 1 nmol) and 3 µl of 30 nmol ADNF, respectively. In this context, colivelin and ADNF were separately dissolved in a saline for the injection. The injection was performed with the cannula in C315IS-4 connected to Hamilton syringe through a cannula tube (C232, PESO/Thin wall, Plastic One).

The motor function (motor performance) was evaluated weekly with a rotarod (CLEA Japan Inc). After the cannulation, the mice were acclimated to the rotarod for 2 days. The mice were placed onto a rotating rod at a speed of 5 rpm, and the time for which each mouse could remain on the rod was automatically detected. The test was conducted according to the protocol wherein the test was completed as a score of 7 minutes if the mouse remained on the rod for 7 minutes (Li M, et al., 2000, Science 288: 335-339; and Kaspar B K, et al., 2003, Science 301: 839-842). Disease onset was defined as the first day when the mouse could not remain on the rotarod for 7 minutes.

Death was defined when the mouse was unable to right itself within 30 seconds after being placed on its back (Li M, et al., op. cit).

(3) Result

Figure 5:
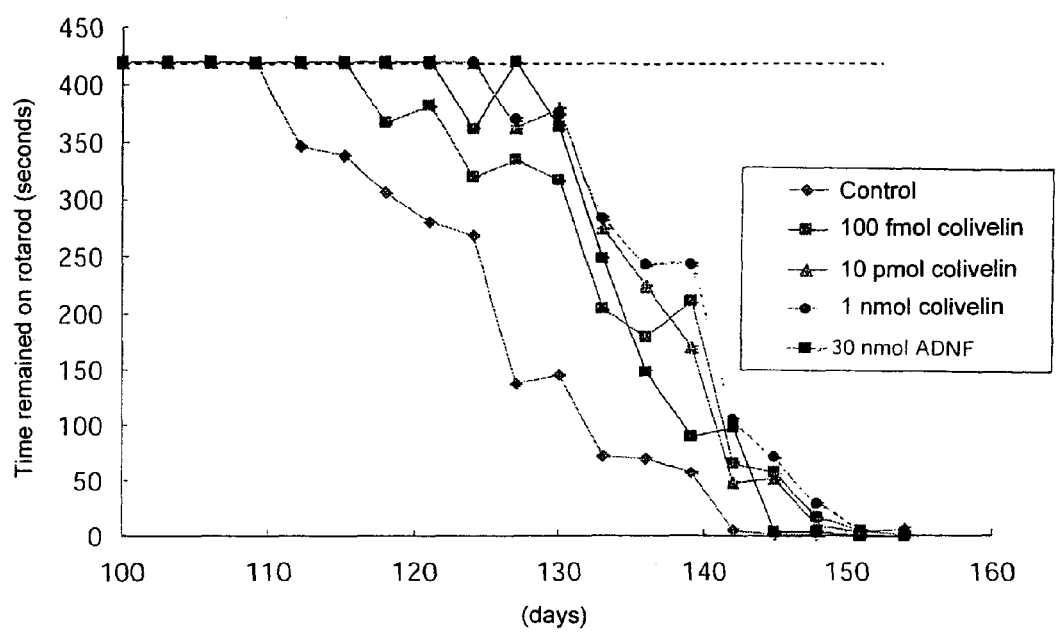
FIG. 5 shows that the intracerebroventricular (icv) administration of colivelin ameliorates the motor function of G93A-SOD1 transgenic mice.

The mice in the control group exhibited the deterioration of motor function in approximately 110 days. Thereafter, motor dysfunction gradually progressed in the mice in the control group. On approximately 140 days, this test became impossible to perform. By contrast, the mice in the ADNF-administered group maintained motor function up to approximately 130 days. The colivelin treatment improved motor function as much as the ADNF treatment did. The 100 fmol colivelin-administered group exhibited the deterioration of motor function in approximately 120 days and could also maintain the motor function until the late stage of the disease by virtue of this treatment. The 1 nmol colivelin treatment exerted the most potent protective action on these model mice and improved motor function (FIG. 5).

The disease onset of the colivelin- or ADNF-treated group exhibited delay as a trend by the treatment (FIG. 6a). The 1 nmol colivelin treatment, which was most potent, resulted in approximately 17-day delay of the onset. The mean survival days of the control group and the ADNF-treated group are 142.7 days and 145.0 days, respectively, showing no difference in viability therebetween (FIG. 6b). The mean survival days of the 100 fmol, 10 pmol, and 1 nmol colivelin-treated groups are 153.3, 159.4, and 156.7 days, respectively, demonstrating the life span-prolonging effect of colivelin treatment. The 10 pmol colivelin treatment was most potent and prolonged their life spans by 11.7%.

Example 4

Icv Administration of Colivelin Improves Spatial Working Memory Impairment Induced by Aβ (25-35)

The icv administration of Aβ peptides has been reported to induce spatial working memory impairment. One icv administration of Aβ (25-35), a neurotoxic region in the Aβ peptide, has been shown to induce spatial working memory impairment in a Y-maze. In this test, the in vivo neuroprotective effect of colivelin on Aβ toxicity was examined.

Male CD-1 mice at 3 months of age were icy-administered once every three weeks with 1 nmol colivelin together with 3 µl of saline or 3 µl of saline alone into the left lateral ventricles. After 1 hour from the first administration of colivelin, 5 µl of saline together with 10 nmol Aβ (25-35) or 5 µl of saline alone was administered to the right lateral ventricles. After 3 weeks from the Aβ peptide administration, each mouse was examined for spatial working memory in a Y-maze. The Y-maze was made of three gray plastic arms (40 cm long, 12 cm high, 3 cm wide at the bottom, and 10 cm wide at the top) connected to each other at angles of 120°. The mice were individually placed at the end of one arm of the Y-maze and allowed to freely explore the arms for 8 minutes. Items examined were (1) frequency of entry into each arm, (2) total arm entry times, (3) spontaneous alternation percentage, and (4) events. The spontaneous alternation percentage was defined as a ratio of the arm choices that differed from the previous two choices ("successful choices") to total choices during the run ("total entry minus two", because the first two choices could not be evaluated for success or failure during the run). For example, if a mouse made 10 entries such as 1-2-3-2-3-1-2-3-2-1, there were five successful choices in eight total choices (10 entries minus two). In this case, the spontaneous alternation percentage was 62.5%.

Figure 7:
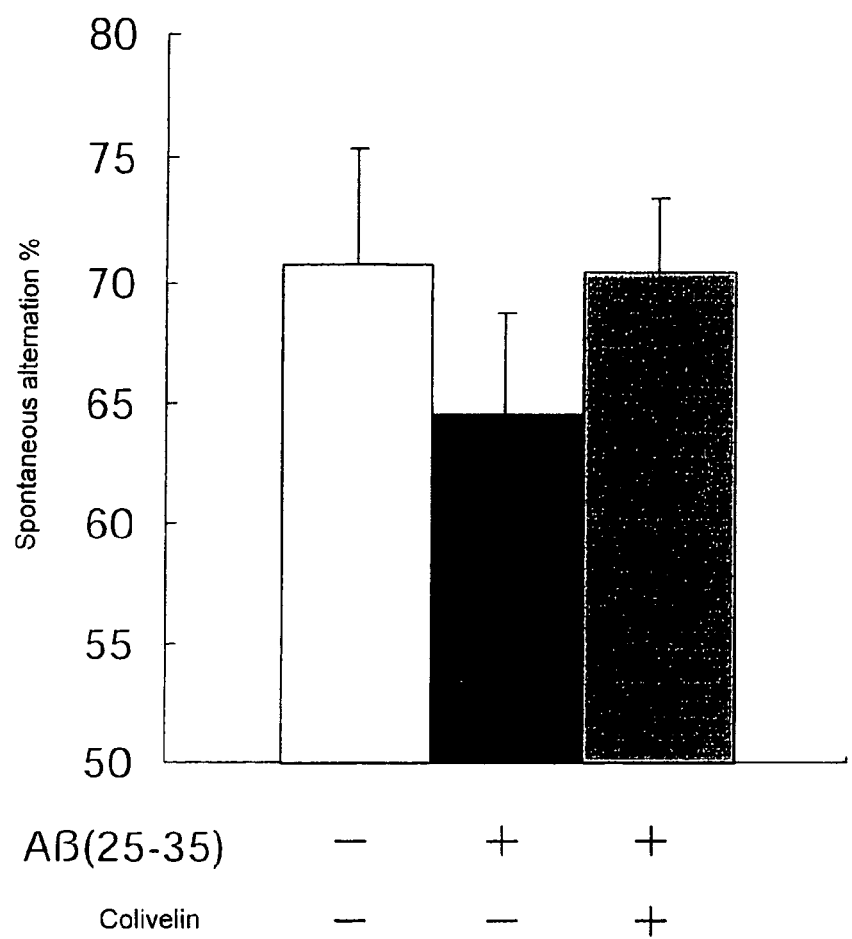
FIG. 7 shows the effect of icv administration of colivelin on the spontaneous alternation percentage in a Y-maze test of mice icy-administered with Aβ (25-35). The data is indicated by mean±SD.

The spontaneous alternation percentage (SA %) of the mice (n=7) treated with neither colivelin nor Aβ (25-35) was approximately 70%, indicating that the spatial working memories of these mice were normal. By contrast, the SA % of the Aβ (25-35)-treated mice was decreased, indicating that Aβ (25-35) impaired their spatial working memories. The colivelin treatment resulted in the recovery of this impairment to 70%, which was the same level as that of the control mice (FIG. 7). These data showed that colivelin protected neurons from toxicity by Aβ (25-35).

Example 5

In Vivo Effect of Colivelin on ALS Mice

Figure 8:
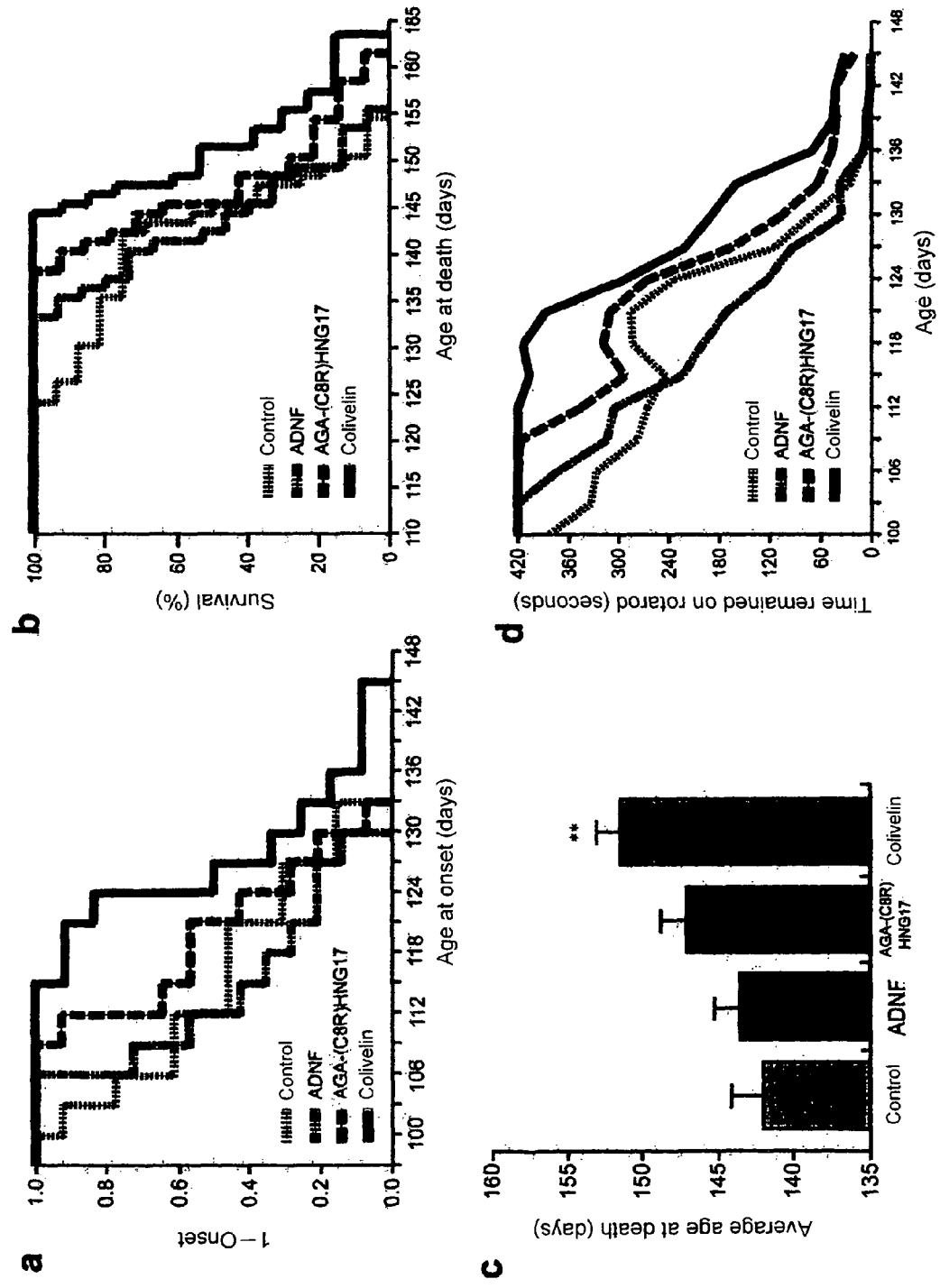
FIG. 8 shows the effect of colivelin on the disease onset (FIG. 8a) and survival (FIG. 8b) of ALS mice in comparison to those of ADNF and AGA-C8R-HNG17. Mice treated with a control (n=16), ADNF (n=15), AGA-C8R-HNG17 (n=14), or colivelin (n=13) were compared by the Kaplan-Meier life test. In addition, the average day of death was compared (FIG. 8c), wherein statistical analysis was conducted by one-way ANOVA, followed by Fischer's PLSD test (**p<0.01). The motor function was evaluated by a rotarod test (FIG. 8d). Mice icy-administered with a control (n=13), ADNF (n=14), AGA-C8R-HNG17 (n=14), or colivelin (n=12) were placed onto a rotating rod at a speed of 5 rpm and observed over max 420 seconds, wherein statistical analysis was conducted by repeatedly measured ANOVA and Fischer's PLSD test. The colivelin-treated mice had motor function significantly better than the motor function of the control mice (*p<0.05)

Cannulas were fixed under aseptic conditions to the left lateral ventricles of G93A-SOD1 Tg mice (ALS model mice, 70-day-old). Colivelin (10 µmol in 3 µl of saline per two days) was icy-injected through the cannulas to compare its protective effect with those of the same amount of ADNF and AGA-C8R-HNG17 (FIG. 8).

The 1-onset (FIG. 8a) and survival (FIG. 8b) of mice treated with a control (n=16), ADNF (n=15), AGA-C8R-HNG17 (n=14), or colivelin (n=13) were compared by the Kaplan-Meier life test. As a result, the colivelin-treated group completely delayed ALS onset up to approximately 114 days, as compared with the ADNF-treated group (approximately 106 days) and the AGA-C8R-HNG17-treated group (approximately 108 days). Regarding survival as well, the colivelin-treated group prolonged the life span of 100% of the mice up to approximately 145 days, as compared with the ADNF-treated group (approximately 133 days) and the AGA-CBR-HNG17-treated group (approximately 138 days). Average age at death was longest in the colivelin-treated mice and was approximately 153 days (FIG. 8c).

Additionally, the motor function was evaluated by the rotarod test (FIG. 8d). Mice treated with a control (n=13), ADNF (n=14), AGA-C8R-HNG17 (n=14), or colivelin (n=12) were placed onto a rotating rod at a speed of 5 rpm and observed over max 420 seconds, wherein statistical analysis was conducted by ANOVA and Fischer's PLSD test. The motor function of the colivelin-treated mouse group was ameliorated most, as compared with those of the ADNF- and AGA-CBR-HNG17-treated groups.

These results showed that colivelin has a more motent neuroprotective effect than those of ADNF and AGA-C8R-HNG17 on G93A-SOD1 that induces toxicity in vivo.

Example 6

Protective Effect of Colivelin on Motor Neuron (1)

Figure 9:
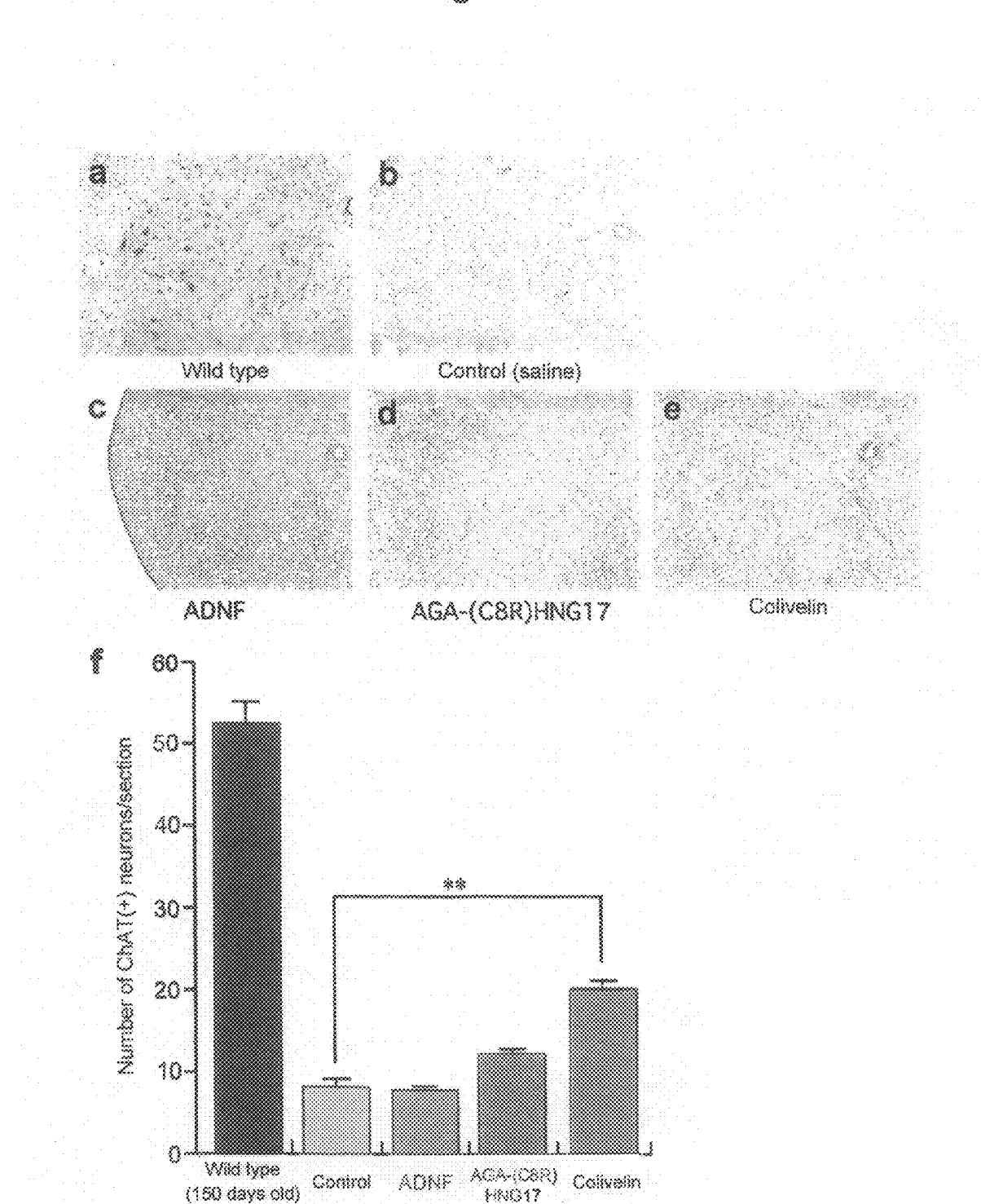
FIG. 9 shows immunohistochemical analysis demonstrating the neuroprotective effect of colivelin. Spinal cord (L1-3) sections from wild-type (n=3, FIG. 9a), control (saline-treated) (n=5, FIG. 9b), ADNF-treated (n=3, FIG. 9c), AGA-C8R-HNG17-treated (n=14, FIG. 9d), or colivelin-treated (n=12, FIG. 9e) mice were immunostained with an anti-ChAT antibody to count ChAT(+) neurons in the ventral gray columns of the spinal cords. The sections were prepared from dead mice. The average number of ChAT(+) neurons per section was compared among the mice (FIG. 9f). Statistical analysis was conducted by one-way ANOVA, followed by Fischer's PLSD test (p<0.01)

The immunohistochemical analysis of neuroprotective effect was conducted using ALS model mice (n=12, FIG. 9e) administered with colivelin, in comparison to wild type (n=3, FIG. 9a), control (saline-treated) (n=5, FIG. 9b), A DNF-treated (n=3, FIG. 9c), and AGA-C8R-HNG17-treated (n=14, FIG. 9d) mice. Spinal cord (L1-3) sections from dead mice in each group were immunostained with an anti-ChAT antibody to count ChAT(+) neurons in the ventral gray column (FIG. 9f).

As a result, the number of ChAT(+) neurons per section in the spinal cord was less than approximately 10 in the control mice, whereas the number of ChAT(+) neurons was approximately 19 in the colivelin-treated mice, indicating that colivelin significantly protected neurons from neurotoxicity and increased the number of ChAT(+) neurons in the spinal cord, albeit in the analysis using the dead mice.

Example 7

Protective Effect of Colivelin on Motor Neuron (2)

Figure 10:
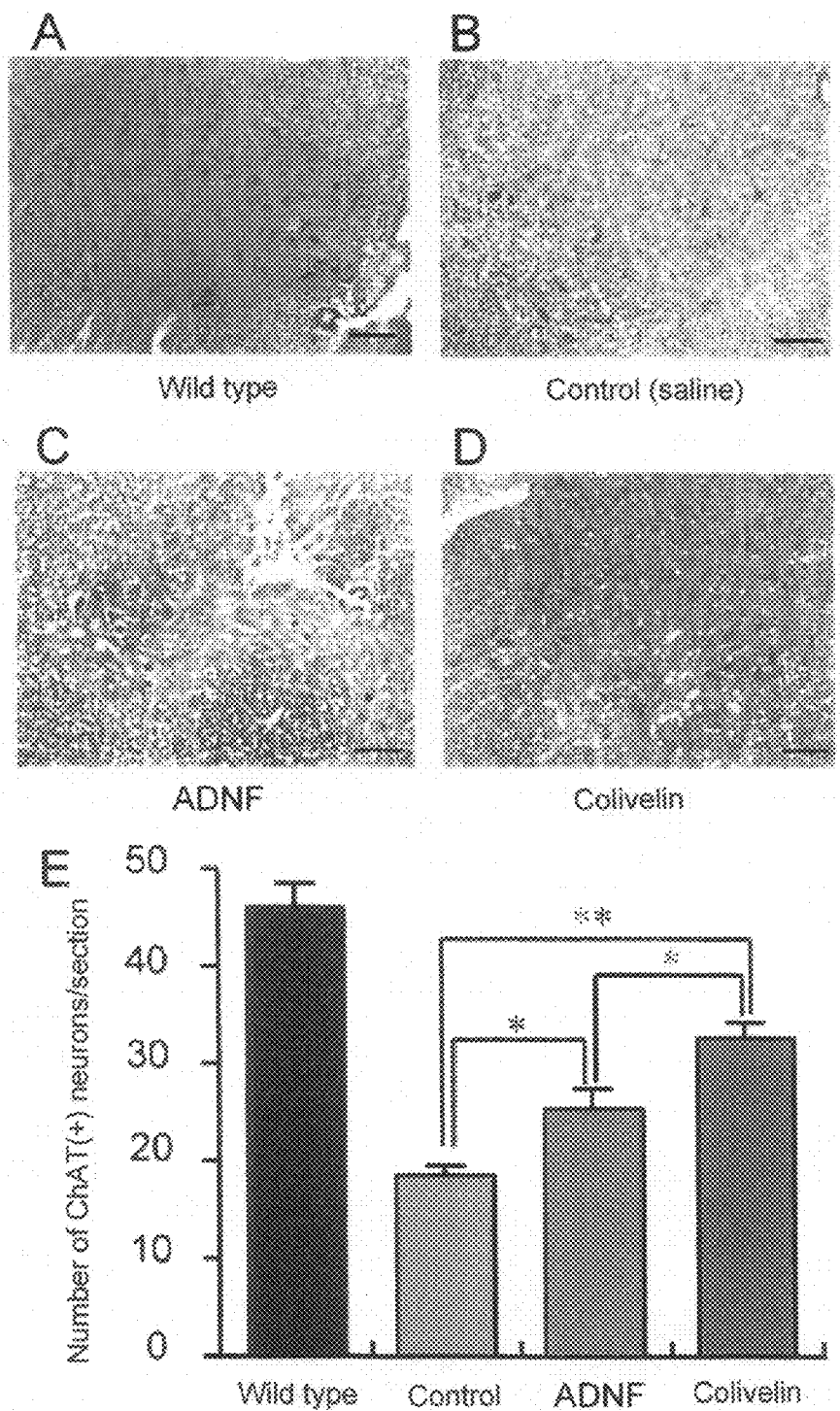
FIG. 10 shows immunohistochemical analysis demonstrating the neuroprotective effect of colivelin. Spinal cord (L1-3) sections from wild-type (n=3, FIG. 10A), control (saline-treated) (n=5, FIG. 10B), ADNF-treated (n=3, FIG. 10C), or colivelin-treated (n=12, FIG. 10D) mice were immunostained with an anti-ChAT antibody to count ChAT(+) neurons in the ventral gray column. The sections were prepared from 120-day-old mice (see FIG. 8d). The average number of ChAT(+) neurons per section was compared among the mice (FIG. 10E). Statistical analysis was conducted by one-way ANOVA, followed by Fischer's PLSD test (p<0.01; *p<0.05).

The immunohistochemical analysis of neuroprotective effect was conducted using ALS model mice (n=12, FIG. 10D) administered with colivelin, in comparison to wild type (n=3, FIG. 10A), control (saline-treated) (n=5, FIG. 10B), and ADNF-treated (n=3, FIG. 10C) mice. Spinal cord (L1-3) sections from the mice in each group were immunostained with an anti-ChAT antibody to count ChAT(+) neurons in the ventral gray column (FIG. 9f). The sections were prepared from 120-day-old mice with motor function increased by colivelin and ADNF (see FIG. 8d)

As a result, the number of ChAT(+) neurons per section in the spinal cord was approximately 19 in the control mice, whereas the number of ChAT(+) neurons was approximately 32 in the colivelin-treated mice, indicating that colivelin significantly protected neurons from neurotoxicity and increased the number or ChAT(+) neurons in the spinal cord.

All publications, patents, and patent applications cited herein are incorporated herein by reference in their entirety.

INDUSTRIAL APPLICABILITY

According to the present invention, the polypeptides of the present invention significantly suppress neuronal cell death and have the effect of delaying the onset of neurodegenerative diseases such as amyotrophic lateral sclerosis and Alzheimer's disease, the effect of ameliorating or improving the motor function of a subject, and the effect of prolonging the life span of a subject. Therefore, the pharmaceutical composition of the present invention is useful for the treatment or prevention of neurodegenerative disease.

The invention claimed is:

1. A pharmaceutical composition for neuroprotection from neuronal cell death in a neurodegenerative disease selected from amyotrophic lateral sclerosis (ALS) or Alzheimer's disease, comprising: (a) an isolated polypeptide comprising the amino acid sequence as defined by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1); or (b) a pharmaceutically acceptable salt of the polypeptide of (a).

2. The pharmaceutical composition according to claim 1, wherein the isolated polypeptide is a dimer.

3. An isolated polypeptide comprising the amino acid sequence as defined by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1), or a salt thereof.

4. The isolated polypeptide according to claim 3, wherein the polypeptide is a dimer.

5. The pharmaceutical composition according to claim 1, comprising approximately 100 fM or a higher concentration of the polypeptide (a).

6. The pharmaceutical composition according to claim 1, comprising the isolated polypeptide consisting of the amino acid sequence as defined by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1).

7. The isolated polypeptide according to claim 3, wherein the isolated polypeptide consists of the amino acid sequence as defined by Ser-Ala-Leu-Leu-Arg-Ser-Ile-Pro-Ala-Pro-Ala-Gly-Ala-Ser-Arg-Leu-Leu-Leu-Leu-Thr-Gly-Glu-Ile-Asp-Leu-Pro (SEQ ID NO: 1).

* * * * *

SEQUENCE LISTING

<160> NUMBER OF SEQ ID NOS: 17

<210> SEQ ID NO 1
<211> LENGTH: 26
<212> TYPE: PRT
<213> ORGANISM: Artificial Sequence
<220> FEATURE:
<223> OTHER INFORMATION: Synthetic peptide

<400> SEQUENCE: 1

Ser Ala Leu Leu Arg Ser Ile Pro Ala Pro Ala Gly Ala Ser Arg Leu
1               5                   10                  15

Leu Leu Leu Thr Gly Glu Ile Asp Leu Pro
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (11)..(11)
<223> OTHER INFORMATION: Xaa at position 11 is Arg or Ala and is part
      of the tetrapeptide Xn1 (residues 11-14)
<220> FEATURE:
<221> NAME/KEY: MUTAGEN
<222> LOCATION: (12)..(12)
<223> OTHER INFORMATION: Xaa at position 12 is Gly or Ala and is part
      of the tetrapeptide Xn1 (residues 11-14)
<220> FEATURE:
<221> NAME/KEY: MUTAGEN
<222> LOCATION: (13)..(13)
<223> OTHER INFORMATION: Xaa at position 13 is Phe or Ala and is part
      of the tetrapeptide Xn1 (residues 11-14)
<220> FEATURE:
<221> NAME/KEY: MUTAGEN
<222> LOCATION: (14)..(14)
<223> OTHER INFORMATION: Xaa at position 14 is Ser or Ala and is part
      of the tetrapeptide Xn1 (residues 11-14)
<220> FEATURE:
<221> NAME/KEY: MUTAGEN
<222> LOCATION: (15)..(15)
<223> OTHER INFORMATION: Xaa represents Cys, Arg, Lys or His
<220> FEATURE:
<221> NAME/KEY: MUTAGEN
<222> LOCATION: (16)..(16)
<223> OTHER INFORMATION: Xaa represents Leu or Arg
<220> FEATURE:
<221> NAME/KEY: MUTAGEN
<222> LOCATION: (17)..(17)
<223> OTHER INFORMATION: Xaa at position 17 is Leu or Ala and is part
      of the dipeptide Xn2 (residues 17-18)
<220> FEATURE:
<221> NAME/KEY: MUTAGEN
<222> LOCATION: (18)..(18)
<223> OTHER INFORMATION: Xaa at position 18 is Leu or Ala and is part
      of the dipeptide Xn2 (residues 17-18)
<220> FEATURE:
<221> NAME/KEY: MUTAGEN
<222> LOCATION: (21)..(21)
<223> OTHER INFORMATION: Xaa represents Gly, L-Ser or D-Ser
<220> FEATURE:
<221> NAME/KEY: MUTAGEN
<222> LOCATION: (22)..(22)
<223> OTHER INFORMATION: Xaa at position 22 is Glu or Ala and is part
      of the tetrapeptide Xn3 (residues 22-25)
<220> FEATURE:
<221> NAME/KEY: MUTAGEN
<222> LOCATION: (23)..(23)
<223> OTHER INFORMATION: Xaa at position 23 is Ile or Ala and is part
      of the tetrapeptide Xn3 (residues 22-25)
<220> FEATURE:

```
<221> NAME/KEY: MUTAGEN
<222> LOCATION: (24)..(24)
<223> OTHER INFORMATION: Xaa at position 24 is Asp or Ala and is part
      of the tetrapeptide Xn3 (residues 22-25)
<220> FEATURE:
<221> NAME/KEY: MUTAGEN
<222> LOCATION: (25)..(25)
<223> OTHER INFORMATION: Xaa at position 25 is Leu or Ala and is part
      of the tetrapeptide Xn3 (residues 22-25)

<400> SEQUENCE: 2

Ser Ala Leu Leu Arg Ser Ile Pro Ala Pro Xaa Xaa Xaa Xaa Xaa Xaa
1               5                   10                  15

Xaa Xaa Leu Thr Xaa Xaa Xaa Xaa Xaa Pro
            20                  25

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (1)..(1)
<223> OTHER INFORMATION: Xaa represents Arg or Ala
<220> FEATURE:
<221> NAME/KEY: MUTAGEN
<222> LOCATION: (2)..(2)
<223> OTHER INFORMATION: Xaa represents Gly or Ala
<220> FEATURE:
<221> NAME/KEY: MUTAGEN
<222> LOCATION: (3)..(3)
<223> OTHER INFORMATION: Xaa represents Phe or Ala
<220> FEATURE:
<221> NAME/KEY: MUTAGEN
<222> LOCATION: (4)..(4)
<223> OTHER INFORMATION: Xaa represents Ser or Ala

<400> SEQUENCE: 3

Xaa Xaa Xaa Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (1)..(1)
<223> OTHER INFORMATION: Xaa represents Glu or Ala
<220> FEATURE:
<221> NAME/KEY: MUTAGEN
<222> LOCATION: (2)..(2)
<223> OTHER INFORMATION: Xaa represents Ile or Ala
<220> FEATURE:
<221> NAME/KEY: MUTAGEN
<222> LOCATION: (3)..(3)
<223> OTHER INFORMATION: Xaa represents Asp or Ala
<220> FEATURE:
<221> NAME/KEY: MUTAGEN
<222> LOCATION: (4)..(4)
<223> OTHER INFORMATION: Xaa represents Leu or Ala

<400> SEQUENCE: 4

Xaa Xaa Xaa Xaa
1

<210> SEQ ID NO 5
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 5

Ser Ala Leu Leu Arg Ser Ile Pro Ala
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Pro Ala Gly Ala Ser Arg Leu Leu Leu Thr Gly Glu Ile Asp Leu
1               5                   10                  15

Pro

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Val Lys Arg Arg Ala
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Arg Gly Ala Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Arg Gly Phe Ser
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Ala Gly Phe Ser
1

<210> SEQ ID NO 11
<211> LENGTH: 4
<212> TYPE: PRT
```

```
<213> ORGANISM: Artificial Sequence
<220> FEATURE:
<223> OTHER INFORMATION: Synthetic peptide

<400> SEQUENCE: 11

Arg Ala Phe Ser
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Arg Gly Phe Ala
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Glu Ile Asp Leu
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Ala Ile Asp Leu
1

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Glu Ala Asp Leu
1

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Glu Ile Ala Leu
1
```

```
<210> SEQ ID NO 17
<211> LENGTH: 4
<212> TYPE: PRT
<213> ORGANISM: Artificial Sequence
<220> FEATURE:
<223> OTHER INFORMATION: Synthetic peptide

<400> SEQUENCE: 17

Glu Ile Asp Ala
1
```